United States Patent [19]

Stjernschantz et al.

[11] Patent Number: 5,422,369
[45] Date of Patent: Jun. 6, 1995

[54] PROSTAGLANDDIN DERIVATIVES FOR THE TREATMENT OF GLAUCOMA OR OCULAR HYPERTENSION

[75] Inventors: Johan W. Stjernschantz; Bahram Resul, both of Uppsala, Sweden

[73] Assignee: Kabi Pharmacia AB, Uppsala, Sweden

[21] Appl. No.: 202,409

[22] Filed: Feb. 25, 1994

Related U.S. Application Data

[63] Continuation of Ser. No. 988,389, Dec. 8, 1992, Pat. No. 5,321,128, which is a continuation of Ser. No. 740,371, Jul. 24, 1991, abandoned, which is a continuation-in-part of Ser. No. 469,442, Apr. 10, 1990, abandoned.

[30] Foreign Application Priority Data

Sep. 6, 1988 [SE] Sweden ................. 8803110
Oct. 28, 1988 [SE] Sweden ................. 8803855

[51] Int. Cl.$^6$ ........................................ A61K 31/557
[52] U.S. Cl. ............................................... 514/530
[58] Field of Search ................................... 514/530

[56] References Cited

U.S. PATENT DOCUMENTS

| | | | |
|---|---|---|---|
| 3,956,284 | 5/1976 | Hess et al. | 260/240 R |
| 3,962,312 | 6/1976 | Hayashi et al. | 260/468 D |
| 3,987,087 | 10/1976 | Bundy | 560/121 |
| 4,001,300 | 1/1977 | Axen | 560/121 |
| 4,011,262 | 3/1977 | Hess et al. | 260/520 B |
| 4,115,586 | 9/1978 | Miller, Jr. | 560/121 |
| 4,116,988 | 9/1978 | Nelson | 260/413 |
| 4,117,119 | 9/1978 | Kurono et al. | 424/180 |
| 4,128,713 | 12/1978 | Schneider | 542/426 |
| 4,131,738 | 12/1978 | Smith | 560/121 |
| 4,599,353 | 7/1986 | Bito | 514/530 |
| 4,820,728 | 4/1989 | Collins et al. | 514/530 |
| 4,824,857 | 4/1989 | Goh et al. | 514/398 |
| 4,883,819 | 11/1989 | Bito | 514/573 |
| 5,001,153 | 3/1991 | Ueno et al. | 514/530 |
| 5,057,621 | 10/1991 | Cooper et al. | 560/53 |

FOREIGN PATENT DOCUMENTS

| | | | |
|---|---|---|---|
| 573018 | 2/1986 | Australia | C07C 177/00 |
| 600168 | 8/1990 | Australia | A61K 31/557 |
| 986926 | 4/1976 | Canada . | |
| 170258 | 2/1986 | European Pat. Off. | C07C 177/00 |
| 242580 | 10/1987 | European Pat. Off. | A61K 31/557 |
| 253094 | 1/1988 | European Pat. Off. | A61K 31/557 |
| 308135A2 | 8/1988 | European Pat. Off. | A61K 31/557 |
| 281239 | 9/1988 | European Pat. Off. | C07C 177/00 |
| 289349 | 11/1988 | European Pat. Off. | C07C 177/00 |
| 308135 | 3/1989 | European Pat. Off. | A61K 31/557 |
| 364417 | 4/1990 | European Pat. Off. | A61K 31/557 |
| 366279 | 5/1990 | European Pat. Off. | A61K 31/557 |
| 455264A2 | 11/1991 | European Pat. Off. | A61K 31/557 |
| 2234709 | 2/1973 | Germany | C07C 57/02 |
| 1324737 | 2/1970 | United Kingdom . | |
| 1324737 | 7/1973 | United Kingdom | C07C 61/00 |

OTHER PUBLICATIONS

Bill A (1975) "Blood Circulation and fluid dynamics in the eye". *Physiol. Rew.* 55: 383–417.

Biological Activities of 17–phenyl–18, 19 20–trinor–prostaglandins in Prostaglandins 9 (1975) 9–18.

Bito L. Z., Camras C. B., Gum G. C. and Resul B. (1989), "The Ocular Hypotensive Effects and Side Effects of Prostaglandins on the Eyes of Experimental Animals" *Progress in Clinical and Biological Research* 312 Ed. L. Z. Bito and Johan Stjernschantz, A. R. Liss Inc., New York.

(List continued on next page.)

*Primary Examiner*—Robert Gerstl
*Attorney, Agent, or Firm*—Kenyon & Kenyon

[57] ABSTRACT

This invention relates a method for topical treatment of glaucoma or ocular hypertension by administration of an effective intraocular pressure reducing amount of a prostaglandin derivative of PGA, PGB, PGE and PGF, in which the omega chain contains a ring structure. The invention further relates to compositions comprising said prostaglandin derivatives in an ophthalmologically compatible carrier.

2 Claims, No Drawings

OTHER PUBLICATIONS

Bito, Baroody and Miranda (1987): Eicosanoids as a new class of ocular Hypotensive agents. The apparent therapeutic advantage of derived Prostaglandins of the A and B type as compared with primary prostaglandins of the E, F and D types", Experimental Eye Research, 44:825.

Supplement to Investigative Ophthalmology and Visual Science 22 39 (1982), L. Z. Bito, A. Draga, J. Blanco, and C. B. Camras, "Maintenance of Reduced Intraocular Pressure (IOP) for several months by topical application of prostaglandin (PG) $E_t$ to Eyes of Trained Cats".

Burke et al., "Prostaglandin $F_{2\alpha}$ Effects on Rabbit IOP Negatively Correlate with Classical $PGF_{2\alpha}$–Receptor Stimulation Presented at ARVO annual meeting in Florida May 1-6, 1988.

Bundy, Chem Abst. 90:168141d, 1979.

Camras C. B., Bito L. Z. (1981). Reduction of intraocular pressure in normal and glaucomatous primate (Aotus trivirgatus) eyes by topically applied prostaglandin $F_{2a}$". *Curr Eye Res* 1:205–209.

Camras, C. B. Podos S. M. Rosenthal J. S. Lee P. Y., Severin C. H. (1987a). Multiple dosing of prostaglandin $F_{2a}$ or epinephrine on cynomolgus monkey eyes. I. Aqueous humor dynamics. *Invest Ophthalmol Vis Sci* 28:463–469.

Camras C. B., Bhuyan K. C. Podos S. M. Bhuyan D. K. Master R. W. P. (1987b) "Multiple Dosing of Prostaglandin $F_{2\alpha}$ or epinephrine on cynomologus monkey eyes. II. Slitlamp biomicroscopy, aqueous humor analysis, and fluorescein angiography." *Invest. Ophthamol. Vis. Sci.* 28:921–926.

Camras C. B. Siebold E. C., Lustgarten J. S., Serle J. B., Frisch S. C., Podos S. M. Bito L. Z. (1988) "Reduction of IOP by prostaglandin $F_{2\alpha}$–1–isopropyl ester topically applied in glaucoma patients", *Ophthalmology* 95(Suppl.) 129.

Camras C. B. Bito L. Z. and Eakins K. E. (1977): "Reduction of intraocular pressure by prostaglandins applied to the eyes of concious rabbits", Invest Ophthamol Vis. Sci. 16:1125.

Crawford K., Kaufman P. L. and True Gabel, B. A. (1987), "Pilocarpine antagonizes $PGF_{2\alpha}$–induced ocular hypotension: Evidence for enhancement of uveoscleral outflow of $PGF_{2\alpha}$". *Invest. Ophthalmol. Vis. Sci.* (Supp.) ARVO Abstracts 11.

Crawford, K. and Kaufman, P. L., (1987) "Pilocarpine Antagonizes Prostaglandin $F_{2\alpha}$–Induced Ocular Hypotension in Monkeys" Arch. Ophthalmology 105 1112.

Flach A. J., Elisason J. A. (1988). "Topical prostaglandin $E_2$ effects on normal human intraocular pressure. *J. Ocu. Pharmacol.* 4:13–18.

Gabelt, B. and Kaufman, P. L. (1989)"Prostaglandin $F_{2\alpha}$ Increases Uvelscleral Outflow in the Cynomologus Monkey", Exp. Eye Res. 49 389–402.

Giuffré (1985). "The Effects of prostaglandin $F_{2\alpha}$ in the human eye." *Graefes Arch Clin. Exp. Ophthalmol.* 222:139–141.

Goldberg I. Kolker A. E. Kass M. A. and Becker B. (1980) "Dipivefrin: current concepts:, australia J. Ophthalmol., 8:147.

Granstrom, E., (1975) "Metabolism of 17--Phenyl-18,19,20-Trinor-Prostaglandin $F_{2\alpha}$ in the Cynomolgus Monkey and the Human Female", *Prostaglandins* 9:19–45.

Kass, M. A., Posos, S. M., Moses, R. A., and Becker B. (1972): Prostaglandin E1 and aqueous humor dynamics", Invest Ophthalmology 11:1022.

Kass, M. A., Mandell Al, Goldberg I., Paine J. M. and Becker B (1979) "Dipivefrin" and epinephrine treatment of elevated intraocular pressure: A comparative Study", Arch Ophthalmol 97:1865.

Kaufman P. L. (1986), "Effects on intracamerally infused prostaglandins on outflow facility in cynomolgus monkey eyes with intact or retrodisplaced ciliary muscle." *Exp. Eye Res.* 43:819–827.

Kerstetter J. R., Brubaker R. F., Wilson S. E., Kullerstrand L. J. (1988). "Prostaglandin $F_{2\alpha}$–1–isopropylester lower intraocular pressure without decreasing aqueous humor flow". *Am. J. Ophthalmol.* 105:30–34.

Kerstetter J. R., Brubaker R. F., Wilson S. E. and Kullerstrand B. S. (1987): "Prostaglandin F2 alpha 1–isopropyl ester effects on aqueous humor dynamics in human subjects". Invest Ophthalmol Vis Sci Suppl, 28:266.

Kerstetter J. R., Brubaker R. F., Wilson S. E. and Kullerstrand L. (1988) "Prostaglandin F2α-1-Isopropylester Lowers Intracolor Pressure Without Decreasing Aqueous Humor Flow". Am. J. Ophthalmology 105:30–34.

(List continued on next page.)

OTHER PUBLICATIONS

Kirk-Othmar "Encyclopedia of Chemical Technology", 3d Ed. Supplement vol. 711-752 (1984).

Lee, P.-Y., Shae H. XZu L., Qu C.-K. (1988). The Effect of prostaglandin $F_{2\alpha}$ on intraocular pressure in normotensive human subjects". *Invest. Ophthalmol. Vis. Sci.* 29:1474-1477.

Miller, "Biological Activities of 17-phenyl-18,19,20-trinorprostaglandins", *Prostaglandins* 9 9-18 (1975).

Nilsson S. F. E., Stjernschantz J. and Bill A. (1987) "$PGF_{2\alpha}$ increase uveoscleral outflow. *Invest. Ophthalmol Vis. Sci. Suppl.* 284.

Prostaglandin $F_{2\alpha}$ Effects on Rabbit IOP Negatively Correlate with Classical $PGF_{2\alpha}$-Receptor Stimulation Presented at AVRO annual meeting in Florida May 1-6, 1988, by Burke et al.

Prostaglandin $F_{2\alpha}$ Effects on IOP Nth Classical $PGF_{2\alpha}$-Receptor Stimulation Presented in Eightly International Congress of Eye Research in San Francisco Sep. 4-8, 1988, by Woodward et al. (Burke is one of the Inventors).

Prostaglandin $F_{2\alpha}$ Effects on Intraocular Pressure Negatively Correlate with FP-Receptor Stimulation Published in Invest. Ophthal. vol. 30 (8) (1989) 1838-1842 by Woodward et al. (Burke is one of the inventors).

Ritch, Shields and Krupin (1989): "The Glaucomas", C. V. Mosby, p. 561.

Starr, M. S. (1971) "Further studies on the effect of prostaglandin on intraocular pressure in the rabit, Exp. Eye, Res 11:170.

Villumsen J. Alm A. (1987): "The effect of prostaglandin $F2\alpha$ eye drops in open angle glaucoma", Invest. Ophthalmol. Vis. Sci. 28:378.

Villumsen J. Alm A. (1989) "Prostaglandin $F_{2\alpha}$ isopropylester eye drops. Effects in normal human eyes." *Br. J. Ophthalmol.* 73:419-426.

Villumser J, Alm A., Soderstrom M. (1989) "Prostaglandin $F2\alpha$-isopropylester Eye Drops: Effect on Intraocular Pressure in Open Angle Glaucoma", Brit. J. Ophthalmology 73, 975-979.

Wang R.-F., Cmamras C. B., Lee P.-Y., Podos S. M. and Bito L. Z. (1987) "The ocular hypotensive effects of Prostaglandins $F2\alpha$ isopropyl ester and A2 in glautomatous monkeys Invest. Ophthalmol Vis Sci ARVO Supl. 28:266.

Woodward et al., "Prostaglandin $F_{2\alpha}$ Effects on IOP Negatively Correlate with Classical $PGF_{2\alpha}$-Receptor Stimulation Presented in Eightly International Congress of Eye Research in San Francisco Sep. 4-8, 1988.

Woodward et al. (1989) "Prostaglandin $F_{2\alpha}$ Effects on Intraocular Pressure Negatively Correlate with FP-Receptor Stimulation" *Invest. Ophthal.* 30 (8) 1838-1842.

Yankee, Chem Abst. 88:62048x, 1978.

Abstracts 12 and 13 on p. 325 of ARVO Annual Meeting Abstract Issue 1988 of Annual Meeting: Sarasota, Fla. May 1-6, 1988.

Abstracts 31, 33 and 35 on p. 35 of Abstracts 8th International Congress of Eye Research, San Francisco, Sep. 4-8, 1988.

Journal of Medicinal Chemistry, vol. 23, 1980, pp. 525-535.

Annual Reports in Medicinal Chemistry, vol. 11, 1976, pp. 80-88.

Zajacz: IRCS Medical Science: Clinical Medicine; Clinical Pharmacology and Therapeutics: Drug Metabolism and Toxicology; The Eye: Reproduction, Obstetrics and Gynecology; vol. 4, 1976, p. 316.

Miranda and Bito: The Ocular Effects of Prostaglandins and Other Eicosanoids, 1989, pp. 171-195.

ASPET abstract: Pharmacologist, vol. 29, 1987, p. 139, 33/187.

Investigative Ophthalmology & Visual Science, vol. 31, 1990, pp. 2560-2567.

The Ocular Effects of Prostaglandins and Other Eicosanoids, 1989, p. 179.

Journal of Ocular Pharmacology, vol. 9, 1991, p. 189.

The Association for Research in Vision and Ophthalmology, Annual Spring Meeting, Sarasota, Fla., May 1-6, 1988: Investigative Ophthalmology & Visual Science, vol. 29, supplement, p. 325, abstracts 12 and 13.

Prostaglandins and Medicine, 3, 1979, pp. 33-37.

Bito: Experimental Eye Research, vol. 39, 1984, pp. 807-829.

Archives of Ophthalmology, vol. 105, 1987, pp. 1036-1039.

Archives of Ophthalmology, vol. 106, 1988, pp. 449-450.

The Ocular Effects of Prostaglandins and Other Eicosanoids, 1989, pp. 349-368.

Investigative Ophthalmology & Visual Science, vol. 25, 1984, 1087-1093.

Prostaglandins, vol. 12, 1976, pp. 493-500.

Prostaglandins, vol. 10, 1975, pp. 5-18.

Arch. Ophthalmol.-vol. 105, Feb. 1987, 249-252.

Exp. Eye Res. (1984) 38, 181-194.

Exp. Eye Res. (1987) 44, 825-837.

ARVO abstracts 266, 5.

PROSTAGLANDDIN DERIVATIVES FOR THE TREATMENT OF GLAUCOMA OR OCULAR HYPERTENSION

This application is a continuation of application Ser. No. 07/988,389, filed on Dec. 8, 1992, now U.S. Pat. No. 5,327,128 which is a continuation of Ser. No. 07/740,371, filed Jul. 24, 1991, now abandoned which is a continuation-in-part of Ser. No. 07/469,442, filed Apr. 10, 1990, now abandoned.

The invention is concerned with new prostaglandin derivatives of PGA, PGB, PGE and PGF, in which the omega chain has been modified with the common feature of containing a ring structure, and their use for the treatment of glaucoma or ocular hypertension. The invention relates also to ophthalmic compositions, containing an active amount of these prostaglandin derivatives, and the manufacture of such compositions.

Glaucoma is an eye disorder characterized by increased intraocular pressure, excavation of the optic nerve head and gradual loss of the visual field. An abnormally high intraocular pressure is commonly known to be detrimental to the eye, and there are clear indications that, in glaucoma patients, this probably is the most important factor causing degenerative changes in the retina. The pathophysiological mechanism of open angle glaucoma is, however, still unknown. Unless treated successfully glaucoma will lead to blindness sooner or later, its course towards that stage is typically slow with progressive loss of the vision.

The intraocular pressure, IOP (abbr. of intraocular pressure) can be defined as according to the formula:

$$IOP = P_e + F \times R$$

where $P_e$ is the episcleral venous pressure, generally regarded as being around 9 mm Hg, F the flow of aqueous humor, and R the resistance to outflow of aqueous humor through the trabecular meshwork and adjacent tissue into Schlemm's canal. Besides passing through Schlemm's canal aqueous humor might also pass through the ciliary muscle into the suprachoroidal space and finally leave the eye through sclera. This uveoscleral route has been described for instance by Bill (1975). The pressure gradient in this case is insignificant compared to the gradient over the interior wall of Schlemm's canal and adjacent tissue in the former case. The flow limiting step along the uveoscleral route is assumed to be the flow from the anterior chamber into the suprachoroidal space.

A more complete formula is given by:

$$IOP = P_e + (F_t - F_u) \times R$$

where $P_e$ and R are defined as above, Ft is the total outflow of aqueous humor and $F_u$ is the fraction passing via the uveoscleral route.

IOP in human beings is normally in the range of 12–22 mm Hg. At higher values, for instance over 22 mm Hg, there is a risk that the eye may be affected. In one particular form of glaucoma, low tension glaucoma, damage may occur at intraocular pressure levels otherwise regarded as physiologically normal. The reason fro this could be that the eye is these individuals is unusually sensitive to pressure. The opposite situation is also known, that some individuals may exhibit an abnormally high intraocular pressure without any manifest defects in the visual field or optic nerve head. Such conditions are usually referred to as ocular hypertension.

Glaucoma treatments can be given by means of drugs, laser or surgery. In drug treatment, the purpose is to lower either the flow (F) or the resistance (R) which, according to formula (1) above, will result in a reduced IOP; alternatively to increase the flow via the uveoscleral route which according to formula (2) also gives a reduced pressure. Cholinergic agonists, for instance pilocarpine, reduce the intraocular pressure mainly by increasing the outflow through Schlemm's canal.

Prostaglandins, which recently have met an increasing interest as IOP-lowering substances may be active in that they will cause an increase in the uveoscleral outflow (Crawford et al, 1987, and Nilsson et al, 1987). They do not appear, however to have any effect on the formation of aqueous humor or on the conventional outflow through Schlemm's canal ((Crawford et al, 1987)

The use of prostaglandins and their derivatives is described for instance in U.S. Pat. No. 4,599,353 (Bito), U.S. Pat. No. 4,883,819 (Bito), U.S. Pat. No. 4,952,581 (Bito), WO89/03384 (Stjernschantz), EP 170258 (Cooper), EP 253094 (Goh, Yasumasa), EP 308135 (Ueno, Ryuzo) and by Bito LZ et al (1983), Camras CB et al (1981, 1987a, 1987b, 1988), Giuffré G (1985), Kaufman PL (1986), Kersetter JR et al (1988), Lee P-Y et al (1988) and Villumsen Jet al (1989).

With respect to the practical usefulness of some of the previously described prostaglandins and derivatives, as suitable drugs for treating glaucoma or ocular hypertension, a limiting factor is their property of causing superficial irritation and vasodilation in the conjunctiva. It is probable, moreover, that prostaglandins have an irritant effect on the sensory nerves of the cornea. Thus local side effects will arise in the eye already when the amounts of prostaglandin administered are quite small—that is, already when the doses are lower than those that would be desirable for achieving maximum pressure reduction. It has thus been found, for instance, that for this reason it is clinically impossible to use $PGF_{2\alpha}$-1-isopropyl ester in the amount that would give maximum pressure reduction. Prostaglandins, being naturally occurring autacoids, are vary potent pharmacologically and effect both sensory nerves and smooth muscle of the blood vessels. Since the effects caused by administrations of $PGF_{2\alpha}$ and its esters to the eye, comprise in addition to pressure reduction also irritation and hyperemia (increased blood flow), the doses currently practicable in clinical tests are necessarily very low. The irritation experienced when $PGF_{2\alpha}$ or its esters are applied, consists mainly in a feeling of grittiness or of having a foreign body in one's eye, this being usually accompanied by increased lacrimation.

We have now found that a solution to the problems discussed above is the use of certain derivatives of prostaglandins A, B, E and F, in which the omega chain has been modified with the common feature of containing a ring structure, for the treatment of glaucoma or ocular hypertension.

The prostaglandin derivatives have the general structure

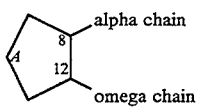

wherein A represents the alicyclic ring $C_8$–$C_{12}$ and the bonds between the ring and the side chains represent the various isomers. In PGA, PGB, PGE and PGF A has the formula

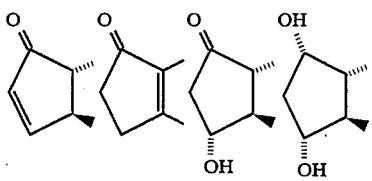

The invention is based on the use of derivatives characterized by their omega chain and various modifications of the alpha chain is therefore possible still using the inventive concept. The alpha chain could typically be the naturally occurring alpha chain, which is esterified to the structure

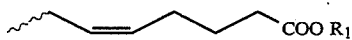

in which $R_1$ is an alkyl group, preferably with 1–10 carbon, especially 1–6 atoms, for instance methyl, ethyl, propyl, isopropyl, butyl, isobutyl, neopentyl or benzyl or a derivative giving the final substance equivalent properties as a glaucoma agent. The chain could preferably be a $C_6$–$C_{10}$ chain which might be saturated or unsaturated having one or more double bonds, and allenes, or a triple bond and the chain might contain one or more substituents such as alkyl groups, alicyclic rings, or aromatic rings with or without hetero atoms.

The omega chain is defined by the following formula:

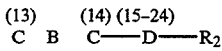

wherein

C is a carbon atom (the number is indicated within parenthesis)

B is a single bond, a double bond or a triple bond

D is a chain with 1–10 carbon atoms, preferably more than 2 and less than 8 atoms, and especially less than 5 atoms. The most efficient derivatives found so far has a chain with 3 atoms. The chain is optionally interrupted by preferably not more than two hetero atoms O, S, or N, the substituents on each carbon atom being H, alkyl groups, preferably lower alkyl groups with 1–5 carbon atoms, a carbonyl group, or a hydroxyl group, whereby the substituent on $C_{15}$ preferably being a carbonyl group, or (R)-OH or (S)-OH: each chain D containing preferably not more than three hydroxyl groups or more than three carbonyl groups, $R_2$ is a ring structure such as a phenyl group which is unsubstituted or has one or more substituents selected from $C_1$–$C_5$ alkyl groups, $C_1$–$C_4$ alkoxy groups, trifluoromethyl groups, $C_1$–$C_3$ aliphatic acylamino groups, nitro groups, halogen atoms, and an phenyl group; or an aromatic heterocyclic group having 5–6 ring atoms, like thiazol, imidazole, pyrrolidine, thiopene and oxazole; or a cycloalkane or a cycloalkene with 3–7 carbon atoms in the ring, optionally substituted with lower alkyl groups withal-5 carbon atoms. Some examples on derivatives which were evaluated are the following (for structure information see Table I):

(1) 16-phenyl-17,18,19,20-tetranor-PGF$_{2\alpha}$-isopropylester (2) 17-phenyl-18,19,20-trinor-PGF$_{2\alpha}$-isopropylester (3) 15-dehydro-17-phenyl-t8,19,20-PGF$_{2\alpha}$-isopropylester (4) 16-phenoxy-17,18,19,20-trinor-PGF$_{2\alpha}$-isopropylester (5) 17-phenyl-18,19,20-trinor PGE$_2$-isopropylester (6) 13,14-dihydro-17-phenyl-18,19,20-trinor-PGA$_2$-isopropylester (7) 15-(R)-17-phenyl-18,19,20-trinor-PGF$_{2\alpha}$-isopropylester (8) 16-[4-methoxy)-phenyl]-17,18,19,20-tetranor-PGF$_{2\alpha}$-isopropylester (9) 13,14-dihydro-17-phenyl-18,19,20-trinor-PGF$_{2\alpha}$-isopropylester

(10) 18-Phenyl-19,20-dinor-PGF$_{2\alpha}$-isopropylester

(20) 19-phenyl-20-nor-PGF$_{2\alpha}$-isopropylester (112) 20-phenyl-PGF$_{2\alpha}$-isopropyl ester (113) 20-(4-phenylbutyl)-PGF$_{2\alpha}$-isopropyl ester (114) 17-(2-thiophene)-18,19,20-trinor-PGF$_{2\alpha}$-isopropyl ester (115) 17-(3-thiophene)-18,19,20-trinor-PGF$_{2\alpha}$-isopropyl ester (116 and 117) 17-R,S-methyl-17-phenyl-18,19,20-trinor-PGF$_{2\alpha}$-isopropyl ester (118) 17-(4-trifluoromethyl phenyl)-18,19,20-trinor-PGF$_{2\alpha}$-isopropyl ester (119) 13,14-dihydro-15-dehydro-17-phenyl-18,19,20-trinor-PGF$_{2\alpha}$-isopropylester (120) 17-(4-methylphenyl)-18,19,20-trinor-PGF$_{2\alpha}$-isopropyl ester (121) 17-(2-methylphenyl)-18,19,20-trinor-PGF$_{2\alpha}$-isopropyl ester (122) 17-(4-fluorophenyl)-18,19,20-trinor-PGF$_{2\alpha}$-isopropyl ester (123) 20-(methylenephenyl)-PGF$_{2\alpha}$-isopropyl ester (124) 17-naphthyl-18,19,20-trinor-PGF$_{2\alpha}$-isopropyl ester (125) 17-cyclohexyl-18,19,20-trinor-PGF$_{2\alpha}$-isopropyl ester (126) 17-(4-methoxyphenyl)-18,19,20-trinor-PGF$_{2\alpha}$-isopropyl ester (127) 17-(3-methoxyphenyl)-18,19,20-trinor-PGF$_{2\alpha}$-isopropyl ester (128) 15-cyclohexyl-16,17,18,19,20-pentanor-PGF$_{2\alpha}$-isopropylester The isopropyl esters have been synthesized in the examples given in this patent application but it should be noticed that the substances disclosed comprises any alkyl ester of the prostaglandin derivatives, preferably with 1–10 carbon atoms and especially with 1–6 atoms, for instance methyl, ethyl, propyl, isopropyl, butyl, isobutyl, neopentyl or benzyl esters.

The most preferred new derivatives at present are those in which the omega chain of the prostaglandin has the 18,19,20-trinor form and especially the 17-phenyl analogues, such as the 15-(R)-, 15-dehydro and 13,14-dihydro-17-phenyl-18,19,20-trinor forms. Such derivatives are represented by (3), (6), (7) and (9) in the formulas given in Table I.

These new derivatives are in general terms described as 17-phenyl-18,19,20-trinor-PGF$_{2\alpha}$-alkyl esters, especially lower alkyl esters with 1-6 carbon atoms, for instance methyl, ethyl, propyl, isopropyl, butyl, isobutyl, neopentyl or benzyl esters.

In the formula given above the most preferred structure at present is obtained when the prostaglandin is a derivative of PGA$_2$, PGE$_2$, and PGF$_{2\alpha}$, B is a single bond or a double bond, D is a carbon chain with 2-5, especially 3 atoms; C$_{15}$ having a carbonyl or (S)-OH substituent and C$_{16}$-C$_{19}$ having lower alkyl substituents, or preferably H, R$_2$ is a phenyl ring, optionally having substituents selected among alkyl and alkyoxy groups.

The invention thus relates to the use of certain derivatives of PGA, PGB, PGE and PGF for the treatment of glaucoma or ocular hypertension. Among these derivatives defined above it has been found that some are irritating or otherwise not optimal, and in certain cases not even useful due to adverse effects and these are excluded in that the group of prostaglandin derivatives defined above is limited to therapeutically effective, that is intraocular pressure or hypertension lowering, and physiologically acceptable derivatives. So is for instance (1) 16-phenyl-17,18,19,20-tetranor-PGF$_{2\alpha}$-isopropylester irritating while this can be eliminated by substituting the phenyl ring with a methoxy group giving formula (8) which represents a therapeutically more useful compound.

The method for treating glaucoma or ocular hypertension comprises contacting an effective intraocular pressure reducing amount of a composition, as aforesaid, with the eye in order to reduce the eye pressure and to maintain said pressure on a reduced level. The composition contains about 0.1-30 μg, especially 1-10 μg, per application of the active substance i.e. a therapeutically active and physiologically acceptable derivative from the group defined above; the treatment may advantageously be carried out in that one drop of the composition, corresponding to about 30 μl, is administered about 1 to 2 times per day to the patients eye. This therapy is applicable both to human beings and to animals.

The prostaglandin derivative is mixed with an ophthalmologically compatible vehicle known per se. The vehicle which may be employed for preparing compositions of this invention comprises aqueous solutions as e.g. physiological salines, oil solutions or ointments the vehicle furthermore may contain ophthalmologically compatible preservatives such as e.g. benzalkonium chloride, surfactants like e.g. polysorbate 80, liposomes or polymers, for example methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

The invention is also related to ophthalmological compositions for topical treatment of glaucoma or ocular hypertension which comprise an effective intraocular pressure reducing amount of a prostaglandin derivative as defined above and an ophthalmologically compatible carrier, the effective amount comprises a dose of about 0.1-30 μ in about 10-50 μg of the composition.

In the experiments carried out in this invention the active compound, in an amount, varying with the potency of the drug, from 30 μg to 300 μg/ml was dissolved in a sterilized aqueous solution (saline 0.9%) containing 0.5% polysorbate-80 as solubilizing agent.

The invention is illustrated by means of the following non-limitative examples, in which 7a and 9a are the at present preferred methods for synthesis of compounds 7 and 9, respectively.

Synthesis of prostaglandin derivatives

EXAMPLE 1 preparation of 16-phenyl-17,18,19,20-tetranor PGF$_{2\alpha}$-isopropyl ester (1)

A 50 ml round bottom flask equipped with a magnetic stirring bar was charged with 17.5 mg (0.04 mmol) 15-phenyl-17,18,19,20-tetranor PGF$_{2\alpha}$ (Cayman Chemical), 5 ml CH$_2$Cl$_2$, 30.2 mg (0.23 mmol) diisopropylethylamine. This solution was stirred at −10° C. and 13.5 mg (0.07 mmol) of isopropyltriflate (freshly prepared) was added. This solution was allowed to stand at −10° C. for 15 min and was then slowly warmed to room temperature. When the esterification was complete according to TLC (usually after 3-4 h at room temperature) the solvent was removed in vacuo. The residue was diluted with 20 ml ethylacetate, washed with 2×10 ml 5% sodium hydrogencarbonate and 2×10 ml 3% citric acid. The organic layer was dried over unhydrous sodium sulfate. The solvent was removed in vacuo and the residue was purified by column chromatography on silica gel-60 using ethyl acetate: aceton 2: 1 as eluent. The title compound was obtained as a colourless oily substance (71% yield).

| Nuclear Magnetic Resonance spectrum (CDCl$_3$)- ppm: δ | |
|---|---|
| 1.2 (6H d) | 3.3 (1H q) |
| 2.8 (2H d) | 5.0 (1H m) |
| 3.8 (1H m) | 5.3-5.7 (4H m) |
| 4.1 (1H t) | 7.1-7.3 (5H m) |

EXAMPLE 2

Preparation of 17-phenyl-18,19,20-trinor PGF$_{2\alpha}$-isopropyl ester (2)

A 50 ml round bottom flask equipped with a magnetic stirring bar was charged whith 20 mg (0.05 mmol) 17-phenyl-18,19,20-trinor PGF$_{2\alpha}$ (Cayman Chemicals), 6 ml acetone, 39.2 mg (0.25 mmol) DBU and 42.5 mg (0.25 mmol) isopropyl iodide. The solution was allowed to stand at room temperature for 24 h, the solvent was removed in vacuo and the residue was diluted with 20 ml of ethyl acetate, washed twice with 10 ml 5% sodiumhydrogen carbonate and 10 ml 3% citric acid. The solvent was removed in vacuo, and the crude product was chromatographed on silica gel-60 using ethyl acetate: acetone 2:1 as eluent. The title compound (2) was obtained as an oily substance (65% yield).

| Nuclear Magnetic Resonance spectrum (CDCl$_3$)- ppm: δ | |
|---|---|
| 1.2 (6H d) | 4.9 (1H m) |
| 3.9 (1H m) | 5.4-5.6 (4H m) |
| 4.1 (1H t) | 7.1-7.3 (5H m) |
| 4.2 (1H m) | |

EXAMPLE 3

Preparation of 15-dehydro-17-phenyl-18,19 20-trinor PGF$_{2\alpha}$-isopropyl ester 20.9 mg (0,092 mmol) DDQ was added to a solution of 10 mg (0,023 mmol) 17-phenyl-18,19,20 trinor PGF$_{2\alpha}$-isopropyl ester (2) in 8 ml dioxane. The reaction mixture immediately turned brown, the reaction mixture was stirred at room temperature for 24 h. The precipitate formed was filtered, washed with 10 ml ethyl acetate, the filtrate was diluted with 10 ml ethylacetate washed with 2×10 ml water, 2×10 ml NaOH IM and 20 ml brine. The organic layer was dried on unhydrous sodium sulfate and the solvent was removed in vacuo, the residue was purified by column chromatography on silica gel using ethyl acetate: ether 1:1 as eluent. The title compound (3) was obtained as a colourless oily substance (76% yield).

| Nuclear Magnetic Resonance spectrum (CDCl$_3$),- ppm: δ | |
|---|---|
| 1.2 (6H d) | 5.4 (2H m) |
| 4.0 (1H m) | 6.2 (1H d) |
| 4.2 (1H m) | 6.7 (1H q) |
| 5.0 (1H m) | 7.1–7.3 (5H m) |

EXAMPLE 4

Preparation of 16-phenoxy-17,18,19,20 -tetranor PGF$_{2\alpha}$-isopropyl ester(4)

Following a procedure similar to that described in example 2 using 20 mg (0.051 mmol) 16-phenoxy-17,18,19,20 -tetranor PGF$_{2\alpha}$ (Cayman Chemicals). The crude product was purified by column chromatography on silica gel-60 using ethyl acetate: acetone 2:1 as eluent. The title compound (4) was an oily substance (53.2% yield).

| Nuclear Magnetic Resonance spectrum (CDCl$_3$)- ppm: δ | |
|---|---|
| 1.2 (6H d) | 5.4 (2H m) |
| 3.9 (3H m) | 5.7 (2H m) |
| 4.2 (1H m) | 6.9 (3H m) |
| 4.5 (1H m) | 7.3 (2H m) |
| 5.0 (1H m) | |

EXAMPLE 15

Preparation of 17-phenyl-18,19,20-trinor PGE$_2$-isopropyl ester (5)

Following a procedure similar to that described in example 2 using 10 mg (0.026 mmol) 17-phenyl-18,19,20-trinor PGE$_2$ (Cayman Chemicals). The crude product was purified by column chromatography on silica gel-60 using ether as eluent. The title compound (5) was an oily substance (38.9% yield).

| Nuclear Magnetic Resonance spectrum (CDCl$_3$)- ppm: δ | |
|---|---|
| 1.2 (6H d) | 5.3 (2H m) |
| 3.9–4.1 (2H m) | 5.6 (2H m) |
| 4.9 (1H m) | 7.2 (5H m) |

EXAMPLE 6

Preparation of 13,14-dihydro-17-phenyl-18,19,20-trinor PGA$_2$-isopropyl ester (6).

Following a procedure similar to that described in example 2 using 10 mg (0.026 mmol) 13,14-dihydro-17-phenyl PGA$_2$ (Cayman Chemicals). The crude product was chromatographed on silica gel-60 using ether as eluent. The title compound was an oily substance (48% yield).

| Nuclear Magnetic Resonance spectrum (CDCl$_3$)- ppm: δ | |
|---|---|
| 1.2 (6H d) | 5.4 (2H m) |
| 4.3 (1H m) | 7.3 (5H m) |
| 5.0 (1H m) | |

EXAMPLE 7

Preparation-of 15-(R)-17-phenyl-18,19,20-trinor PGF$_{2\alpha}$-isopropyl ester (7) (Table II)

7.1 Preparation of 1-(S)-2-oxa-3-oxo-6-(R)-(3-oxo-5-phenyl-1-trans-pentenyl)-7-(R)-(4-phenylbenzoyloxy)-cis-bicyclo [3,3,0]octane (13)

18 g (0.05 mol) alcohol (11), 32 g (0.15 mol) DCC, 39.1 g (0.5 mol) DMSO (newly distilled from CaH$_2$) and 30 ml DME were charged to a 200 ml flask under nitrogen. 0.49 g (0.005 mol) of orthophosphoric acid was added in one portion, and an exothermic reaction occured. The reaction mixture was stirred mechanically at room temperature for 2 h, and the resultant precipitate was filtered and washed with DME. The filtrate (12) can be used directly for Emmon condensation reaction.

To a suspension of 1.2 g (0.04 mol) NaH (80% washed with n-pentane to remove mineral oil) in 100 ml DME under nitrogen was added dropwise 12.3 g (0,048 mol) dimethyl-2-oxo-4-phenylbutyl-phosphonate in 30 ml DME. The mixture was stirred mechanically for 1h at room temperature, then cooled to −10° C. and a solution of the crude aldehyde (12) was added in dropwise. After 15 min at 0° C. and 1 h at room temperature the reaction mixture was neutralized with glacial acetic acid, the solvent was removed under vacuum, and to the residue was added 100 ml ethyl acetate, washed with 50 ml water and 50 ml brine. The organic layer was dried over unhydrous sodium sulfate. The solvent was removed in vacuo and the resulting white precipitate filtered and washed with cold ether. The title compound (13) was obtained as a crystalline substance mp 134.5-135.5 (53% yield).

7.2 Preparation of 1-(S)-2-oxa-3oxo-6-(R)-[3-(R,S)-hydroxy-5-phenyl-1-trans-pentenyl]-7-(R)-(4-phenylbenzoyloxy) cis-bicyclo [3,3,0]octane (14)

10 g (0.021 mol) enone (13) and 3.1 g (0,008 mol) cerous-chloride heptahydrate in 50 ml methanol and 20 ml CH$_2$Cl$_2$ were charged to a 200 ml round bottom flask equipped with a magnetic stirring bar and was cooled to −78° C. under nitrogen. 0.476 g (0.012 mol) of sodium borohydride was added in small portions, after 30 min the reaction mixture was quenched by addition of saturated NH$_4$Cl, and extracted with 2×50 ml ethyl acetate. The extracts were dried and concentrated to leave a colourless oil (98% yield).

7.3 Preparation of 1-(S)-2-oxa-3-oxo-6-(R)-[3-(R,S)-hydroxy-5-phenyl-1-trans-pentenyl]-7-(R)-hydroxy-cis-bicyclo-[3,3,0]octane (15)

To a solution of 9.8 g (0.02 mol) lactone (14) in 100 ml absolute methanol was added 1.7 (0,012 mol) potassium carbonate. The mixture was stirred with a magnetic bar, at room temperature. After 3 h the mixture was neutralized with 40 ml HCl 1 M, and extracted with 2×50 ml ethyl acetate. The extracts were then dried on unhydrous sodium sulfate and concentrated. The crude product was chromatographed on silica gel using ethyl acetate: acetone as eluent. The title compound (15) was obtained as an oily substance (85% yield).

7.4 Preparation of 1-(S)-2-oxa-3-hydroxy-6-(R)-[3-(R,S)-hydroxy-5-phenyl-1-trans-pentenyl]-7-(R)-hydroxy-cis-bicyclo[3,3,0]octane (16)

To a solution of 3g (0.011 mol) lactone (15) in 60 ml unhydrous THF, stirred magnetically and cooled to −78° C., 4.5 g (0.0315 mol) DIBAL-H in toluene was added dropwise. After 2 h the reaction mixture was quenched by addition of 75 ml methanol. The mixture was filtered, the filtrate was concentrated in vacuo and the residue was chromatographed on silica gel-60 using ethyl acetate: acetone 1:1 as eluent. The Title compound (16) was obtained as a semisolid substance (78% yield).

7.5 Preparation of 15-(R,S)-17-phenyl-18,19,20-trinor $PGF_{2\alpha}$ (17)

2.5 g (25 mmol) sodium methyl sulfinylmethide in DMSO (freshly prepared from sodium anhydride and DMSO) was added dropwise to a solution of 5.6 g (12.6 mmol) 4-caboxybutyl triphenyl-phosphonium bromide in 12 ml DMSO. To the resultant red solution of the ylide was added dropwise a solution of the 1.2 g (4.2 mmol) hemiacetal (16) in 13 ml DMSO, and the mixture was stirred for 1 h. The reaction mixture was diluted with 10 g ice and 10 ml water and extracted with 2×50 ml ethyl acetate, whereafter the aqueous layer was cooled, acidified with HCl 1 M and extracted with ethyl acetate, and then the organic layer was dried and concentrated. The resulting crude product was a colourless substance. The purity of the title compound (17) was estimated by TLC on silica gel using ethyl acetate: acetone: acetic acid 1:1:0.2 v/v/v as eluent.

7.6 Preparation of 15-(R)-17-phenyl-18,19,20-trinor $PGF_{2\alpha}$-isopropyl ester (7)

The crude product (17) was esterified following a procedure similar to that described in example 2 the product was purified by column chromatography on silica gel-60 using ethyl acetate as eluent and the resulting mixture of $C_{15}$ epimeric alcohol were separated.

The title compound (7) was obtained as a colourless oily substance (46% yield).

| Nuclear Magnetic Resonance spectrum (CDCl$_3$),- ppm: $\delta$ | |
| --- | --- |
| 1.2 (6H m) | 5.4 (2H m) |
| 3.9 (1H m) | 5.6 (2H m) |
| 4.15 (2H m) | 7.2 (5H m) |
| 4.95 (1H m) | |

EXAMPLE 7a: SCHEME 1

Preparation of 15-R-17-phenyl-18,19,20-trinor, $PGF_{2\alpha}$-isopropylester 7

Step a

7a-1: Preparation of 1-(S)-2-oxa-3-oxo-6R-formyl-7R-(4-phenylbenzoyloxy) cis-bicyclo-[3,3,0]-octane A mixture of alcohol 28 (20 g, 56, 8 mmol), DCC (35, 1 g, 170,0 mmol), DMSO (35,5 g, 454 mmol) and DME (80 ml) was stirred mechanically under nitrogene at ambient temperature for 5 min, [1] and thereafter one portion of orthophosphoric add 85% (3,3 g, 28,4 mmol) was added. After stirring for 2 h, at which time the reaction was completed (TLC monitoring), the resultant precipitate was filtered off and washed with DME to give the unstable crude aldehyde 2. R$_f$=0,32 (silica gel, EtoAc:toluene 2:1).

Step b

7a-2: Preparation of 1-(S)-2-oxa-3-oxo-6R-[3-oxo-5-phenyl-1-transpentenyl]-7R-(4-phenylbenzoyloxy) cis-bicyclo-[3,3,0]-octane 30

To a suspension of NaH (2,2 g, 74 mmol) (80% washed with n-pentane to remove mineral oil) in DME (150 ml) under nitrogene, was added dropwise dimethyl-2-oxo-4-phenyl-butyl-phosphonate (20,9 g, 81,6 mmol) prepared according to the method described by Corey et al [2], in DME (50 ml) and stirred mechanically for 1 h at room temperature. The mixture was then cooled to −10° C. and a solution of the crude aldehyde 29 was added dropwise. After 15 min at 0° C. and 1 h at room temperature (TLC monitoring) the reaction mixture was neturalized with glacial acetic acid, the solvent was removed and to the residue was added ethyl acetate (150 ml), washed with water (50 ml) and brine (50 ml). The organic layer was dried over unhydrous sodium sulfate. This solvent was then removed in vacuo and the resulting white precipitate was filtered and washed with cold ether. The title compound 3 was a crystaline substance mp 134–135,5; yield=28 g (63%); R$_f$=0,55 (silica gel, EtoAc:toluene 2:1)

$[\alpha]^{20}{}_D$= −116 (C=1,26 CH$_3$CN)

$^1$H-NMR (CDCl$_3$/TMS): $\delta$=2,9 (8Hm), 5,1 (1H t), 5,3 (1H m), 6,2 (1H d), 6,7 (1H dd), 7,1–7,6 (10H m), 8,1 (4H d).

Step c

7a-3: Preparation of 1-(S)-2-oxa-3-oxo-6R-(3R,S-3-hydroxy-5-phenyl-1-pentenyl)-7R-(4-phenylbenzoyloxy)cis-bicyclo-[3,3,0]-octane 31

To a stirred mixture of fie above lactone 30 (16 g, 33,2 mmol) and cerous chloride heptahydrate (4,9 g, 13,28 mmol) in methanol: dichloromethene 2:1 (100 ml) at $\sim$ −10° C. was added sodium borohybride (0,63 g, 17,2 mmol) in small portions, and after 30 min (TLC monitoring), the reaction mixture was quenched by addition of 1N HCl and extracted with ethyl acetate (2×100 ml). After drying over anhydrous sodium sulfate, concentration in vacuo the corresponding epimeric mixture of alcohols was obtained as a colourless oil; yield=15,6 g (96%); R$_f$=(silica gel, EtoAc:hexane 3:1)

$^1$H-NMR, (CDCl$_3$/TMS): $\delta$=3,7(1H m), 5,1 (1H m), 5,3 (1H m), 7,2 (5H m), 7,4 (3H m), 7,6 (4H m), 8,1 (2H d).

Step d

7a-4: Preparation of 1-(S)-2-oxa-3-oxo-6R-(3R,S-hydroxy-5-phenyl-1-pentenyl)-7R-hydroxy-cis-bicyclo-[3,3,0]-octane 32

To a solution of lactone 31 (13 g, 26,7 mmol) in methanol (50 mi) was added potassium carbonate (1,9 g, 13, 3 mmol) with stirring at ambient temperature for 3 h (TLC monitoring). The mixture was acidified to pH 4 with 1 N HCl, and the product extracted with ethylacetate (2×75 ml), where upon the organic phase was dried and evaporated to dryness. The crude product was subjected to flash column chromatography (silica gel, ethylacetate; acetone 1:1), giving the product 32 as a colourless oil with a yield=5,8 g (72%); $R_f$=(silica gel, EtoAc:acetone 3:1)

$^1$H-NMR (CDCl$_3$/TMS): δ=1,4 (2H m), 1,7 (4H m), 2,7 (4H m), 3,6 (1H m), 3,9 (1H m), 4,9 (1H t), 7,2 (5H m).

Step e 7a-5: Preparation of 1-(S)-2-oxa-3-oxo-6R-[3R,S-(2-tetrahydropyranyloxy)-5-phenyl-1-pentenyl]-7R-7-(2-tetrahydropyranyloxy)-cis-bicyclo-[3,3,0]-octane 33

To a stirred solution of alcohol 32 (4,3 g, 14 mmol), dihydropyran (4,7 g, 56 mmol) in dichloromethane (30 ml) under nitrogene was added pyridinium-4-toluene sulfonate (0,35 g, 1,4 mmol). The mixture was then allowed to stand at room temperature for 12 h (TLC monitoring) where upon the solution was quenched with methanol (10 ml) and the solvent removed in vacuo. The residue was diluted with ethylacetate (100 ml), washed with 5% cold sodium hydrogen carbonate (30 ml), and finally brine (30 ml) whereafter it was concentrated in vacuo. The crude product 16 was used directly for the next step. $R_f$=(silica gel, ethyl acetate).

Step f 7a-6: Preparation of 1-(S)-2-oxa-3-hydroxy-6R-[3R,S-(2-tetrahydropyranyloxy)-5-phenyl-1-pentenyl]-7R-(2-tetrahydropyranyloxy)-cis-bicyclo-[3,3,0]-octane 34

To a stirred solution of the above lactone 33 (3,6 g, 7,8 mmol) in dry toluene (60 m]) at −78° C. was added a solution of diisobutylalbuminium hydride (1,5 M i tolulene. 1,3 g, 9,3 mmol) dropwise. After stirring for 2 h (TLC monitoring) the reaction mixture was quenched by addition of methanol (60 ml). The temperature was raised to room tmeperature and stirring continued for 3.4 h. After filtration, the filtrate was concentrated in vacuo. The corresponding lactol 9 was obtained as a colourless oil. Yield=2,5 g (76%). $R_f$=0,47 (silica gel, EtoAc).

Step g 7a-7: Preparation of 11,15-bistetrahydropyranyloxy-15R,S-17-phenyl-18,19,20-trinor-PGF$_{2α}$35

Sodium methylsulfinylmethide (2,7 g, 27,2 mmol) freshly prepared from sodium hydride and DMSO was added dropwise to a solution of 4-carboxybutyl triphenylphosphonium bromide (3,7 g, 13,7 mmol) in DMSO (40 ml). To the resultant red solution of ylide was added dropwise a solution of the lactol 34 (1,5 g, 3,9 mmol) in DMSO (15 ml) and the mixture was stirred for 1 h (TLC monitoring). The reaction mixture was diluted with ice and water (50 ml), acidified with 1 N HCl and extracted with ethyl acetate, where upon the oganic layer was dried over (Na$_2$SO$_4$), and concentrated in vauco furnishing 10 as a slightly yellow oil which is used directly for the next step.

$R_f$=0,3 (silica gel, EtoAc).

Step h 7a-8: Preparation of 11,15-bistetrahydropyranyloxy-15R,S-17-phenyl-18,19,20-trinor-PGF$_{2α}$-ipr ester 36

To a stirred solution of the crude product 35 (2,2 g, 3,9 mmol) in acetone (25 ml) at ±0° C., was added DBU (4,2 g, 27,0 mmol) dropwise, and the mixture was allowed to warn up to room temperature, followed by dropwise addition of isopropyl iodide (4,9 g, 23,5 mmol) with continuously stirring for 4 h (TLC monitoring). The mixture was transferred to a separatory funnel, diluted with ether (100 ml), washed with brine (30 ml), citric acid 3% (2×25 ml) and sodium hydrogen carbonate 5% (2×25 ml), dried (Na$_2$SO$_4$) and evaporated. After flash column chromatography (silica gel, ether) the corresponding ester 36 was obtained as a colourless oil; yield=2,0 g (57%).

Step j 7a-9: Preparation of 15-1R-17-phenyl-18,19,20-trinor-PGF$_{2α}$-isopropyl ester 7

To a stirred solution of the above ester 36 (1,97 g, 3,28 mmol) in ethanol (25 ml) was added pyridinium-4-toluenesulfonate (0.1% 0.33 mmol) and the mixture was warmed to 50° C. over a period of 3 h at which time the reaction was complete (TLC monitoring). The mixture was concentrated in vauco, the residue diluted with ethyl acetate (40 ml), washed with water (20 ml) and thereafter brine (20 ml). The organic layer was dried. The epimeric mixture was separated by flash chromatograhy (silica gel, ethyl acetate ) the pure isomers 2 and 7 were obtained as a colourless oil Isomer 7 yield 0,3 g. Isomer 2 yield=0,25 g Isomer 7[α]$^{20}$$_D$=+23° (C=0,6 CH$_3$CN).

TLC Isomer 2: $R_f$=0,23 (silica gel, ethyl acetate).
TLC Isomer 7: $R_f$=0,28 (silica gel, ethyl acetate).

$^1$H-NMR (CDCl$_3$/TMS): δ=1,2 (6H d), 1,6–1,9 (6H m), 2,1 (4H t), 2,6–2.9 (4H m), 3,9 (1H m), 4,2 (2H m), 5,0 (1H m), 5,4 (2H m), 5,6 (2H m), 7,2 ( 5H m).

EXAMPLE 8

Preparation of 16-[4-(methoxy)phenyl]-17,18,19,20-tetranor PGF$_{2α}$-isopromyl ester (8)

Following a procedure similar to that described in example 7 with modified step 7-2, the aldehyde 12 described in step 7-2 was reacted with dimethyl-2-oxo-3-[4-(methoxy)phenyl]-propylphosphonate and was purified by column chromatography on silica gel-60 using ethyl acetate: toluene 1:1 as eluent. A colourless oily substance was obtained (57% yield).

The title compound 16-[4-(methoxy)phenyl]-17,18,19,20-tetranor PGF$_{2α}$-isopropyl ester (8) was obtained as an oily substance, and purified by column chromatography on silica gel-60 using ethyl acetate as eluent (46% yield).

| Nuclear Magnetic Resonance spectrum (CDCl$_3$)- ppm: δ | |
|---|---|
| 1.2 (6H d) | 5.0 (1H m) |
| 2.8 (2H d) | 5.4 (2H m) |
| 3.75 (3H S) | 5.6 (2H m) |
| 3.9 (1H m) | 6.8 (2H d) |
| 4.15 (1H m) | 7.2 (2H d) |

| Nuclear Magnetic Resonance spectrum (CDCl$_3$)- ppm: δ |
|---|
| 4.3 (1H m) |

EXAMPLE 9

Preparation of 13,14-dihydro-17-phenyl-18,19,20-trinor PGF$_{2\alpha}$-isopropylester (9)

Following a procedure similar to that described in example 7, with minor modification, 5 g (0,018 mol) enone (13) in 100 ml THF was reduced using 2.03 g 10% pd/c under hydrogen atmosphere. After completion of the reaction (as determined by TLC on silica gel using ethylacetate: toluene 1:1 as eluent) The mixture was filtered on celite. The filtrate was concentrated in vacuo and an oily substance was obtained (86% yield).

The final product 13,14-dihydro-17-phenyl-18,19,20-trinor PGF$_{2\alpha}$-isopropyl ester containing a mixture of C$_{15}$ epimeric alcohols were separated by preparative liquid chromatography using 40% CH$_3$CN in water v/v as eluent.

| Nuclear Magnetic Resonance spectrum (CDCl$_3$)- ppm: δ | |
|---|---|
| 1.2 (6H d) | 5.0 (1H m) |
| 3.6 (1H m) | 5.4 (2H m) |
| 3.9 (1H m) | 7.2 (5H m) |
| 4.15 (1H m) | |

EXAMPLE 9a SCHEME 2

Preparation of 13,14-dihydro-17-phenyl-18,19,20-trinor-PGF$_{2\alpha}$-isopyropyl ester. 9

Step k 9a-1 Preparation of 1-(S)-2-oxa-3-oxo-6R-(3S-hydroxy-5-phenyl-1-tran-spentenyl)-7R-(4-phenylbenzoyloxy) cis-bicyclo-[3,3,0]-octane 38

To a stirred solution of lithium tri-sec-butylborohybride (0,5 g, 13,55 mmol) [4] in dry ether (30 ml) at −120° C. under nitrogen was a solution of enone 30 (5 g, 10,325 mmol) (in THF: ether 1:1) (20 ml) cooled to −78° C. within a period of one minute after TLC monitoring (1 h) added. The reaction mixture was powered into a mixture of water, sodium bisulphate and brine. The temperature was raised to ±0° C., more water added, and the mixture transferred to a separatory funnel. Ethyl acetate (50 ml) was added. The organic phase was dried (Na$_2$SO$_4$), concentrated and subjected to flash column chromatography (silica gel, ethyl acetate) furnishing 38 as a white crstalline product; yield = 3 g (60%); R$_f$=0,5 (silica gel, EtoAc).

[α]$^{25}$$_D$= −101,59 (C=0,69 CH$_3$CN).

$^1$H-NMR (CDCl$_3$/TMS): δ=4,1 (1H m), 5,5 (2H m), 5,3 (1H m), 7,1–7.6 (10H m), 8,1 (4H d).

Step l 9a-2 Preparation of 1-(S)-2-oxa-3-oxo-6R-(3S-hydroxy-5-phenyl-1-transpentenyl)-7R-hydroxy) cis-bicyclo-[3,3,0]-octane 39

To a solution of lactone 38 (9,8 g, 20,0 mmol) in methanol (100 ml) was added potassium carbonate (1,7 g, 12 mmol), and stirred at ambient temperature for 3 h (TLC monitoring). The mixture was neutralized with 1 N HCl (40 ml) and the product extracted with ethyl acetate (2×50 ml). The organic phase was dried (Na$_2$SO$_4$) and evaporated to dryness. The crude product was subjected to flash column chromatography (silica gel, ethyl acetate:acetone 1:1). The title compund 39 was obtained as a colourless oil; yield=4,9 g (85%). R$_f$=0,31 (silica gel, EtoAc).

[α]$^{20}$$_D$= −20,48 (C=2,5 CH$_3$CN).

$^1$H-NMR(CDCl$_3$/TMS): δ=1,9(2H m), 2,7 (4H m), 3,9 (1H m), 4,1 (1H m), 4,9 (1H m), 5,5 (2H m), 5,6 (1H m), 7,2 (5H m).

Step m 9a-3 Preparation of 1-(S)-2-oxa-2-oxo-6R-[3S-(2-tetrahydropyranyloxy)-5-phenyl-1-trans-pentenyl]-7R-(2-tetrahydropyranyloxy)-cis-bicyclo-[3,3,0]-octane 40

To a stirred solution of DIOL 39 (3,3 g, 11,6 mmol) and dihydropyran (4,4 g, 52 mmol) in dichloromethane (50 ml) under nitrogen was added pyridinium-4-toluenesulfonate (0,3 g, 1,15 mmol). The mixture was allowed to stand at room temperature for 16 h (TLC monitoring), the solution was remoded in vacuo. The residue was diluted with ether (100 ml), transferred to a separatory funnel, and washed with brine (30 ml), where upon the organic layer was dried (Na$_2$SO$_4$). When concentrated in vacuo 40 was obtained as a colourless oil, which was used directly for the next step.

R$_f$=0,57 (silica gel, ether).

Step n 9a-4 Preparation of 1-(S)-2-oxa-3-oxo-6R-[3R-(2-tetrahydropyranyloxy)-5-phenyl-1-pentenyl]-7R-(2-tetrahydropyranyloxy)-cis-bicyclo-[3,3,0 ]octane 41

The above lactone 40 (5,5 g, 11,7 mmol) was dissolved in THF or ethanol (100 ml) and stirred under hydrogene atmosphere for 4 h (TLC monitoring) in the presence of Pd-c catalyst (2,1 g). Filtration through celite pad followed by concentration gave pure 41 as a colourless oil which was used directly for the next step; yield=5,3 g (97%); R$_f$=0,39 (silica gel, ether:ethyl acetate:acetic acid 50:1:0,2).

$^1$H-NMR (CDCl$_3$/TMS): δ=4,6 (1H m), 4,9 (1H m), 7,2 (5H m).

Step o 9a-5 Preparation of 1-(S)-2-oxa-3-hydroxy-6R-[3R-(2-tetrahydropyranyloxy)-5-phenyl-1-pentenyl]-7R-(2-tetrahydropyranyloxy)-cisbicyclo-[3,3,0]-octane 42

To a stirred solution of the above lactone 41 (5,5 g, 11,7 mmol) in dry toluene (60 ml) at −78° C. was added a solution of diisobutyalbumiun hybride (1,5 M i toluene. 2,0 g, 14,0 mmol) dropwise. After stirring for 2 h (TLC monitoring) the reaction mixture was quenched by addition of methanol (60 ml). The temperature was raised to room temperature and stirring continued for 3.4 h. After filtration, the filtrate was concentrated in vacuo. The corresponding lactol 42 was obtained as a colourless oil; yield=3,8 g (76%); R$_f$=0,42 (silica gel, EtoAc).

Step p

9a-6 Preparation of 11,15-bistetrahydropyranyloxy-13,14-dihydro-17-phenyl-18,19,20-trinor-PGF$_{2\alpha}$ 43

Sodium methylsulfinylmethide (4,1 g, 40,9 mmol) freshly prepared from sodium hybride and DMSO was added dropwise to a solution of 4-carboxybutyl triphenylphosphonium bromide (5,5 g, 20,5 mmol) in DMSO (40 ml). To the resultant red solution of ylide was added dropwise a solution of the lactol 42 (2,3 g, 5,9 mmol) in DMSO (15 ml) and the mixture was stirred for 1 h (TLC monitoring). The reaction mixture was diluted with ice and water (50 ml), acidified with 1 N HCl and extracted with ethyl acetate, where upon the organic layer was dried over (Na$_2$SO$_4$), and concentrated in vacuo furnishing 43 as a slightly yellow oil which is used directly for the next step.

R$_f$=0,38 (silica gel, EtoAc).

Step q

9a-7 Preparation of 11,15-bistetrahydropyranyloxy-13,14-dihydro-17-phenyl-18,19,20-trinor-PGF$_{2\alpha}$-isopropyl ester 44

To a stirred solution of the crude product 43 (3,27 g, 5,9 mmol) in acetone (25 ml) at ±0° C., was added DBU (6,25 g, 41,0 mmol) dropwise, and the mixture was allowed to warm up to room temperature, followed by dropwise addition of isopropyliodide (7,3 g, 35,2 mmol) with continuously stirring for 4 h (TLC monitoring). The mixture was transferred to a separatory funnel, diluted with ether (100 ml), washed with brine (30 ml), citric acid 3% (2×25 ml) and sodium hydrogen carbonate 5% (2×25 ml), dried (Na$_2$SO$_4$) and evaporated. After flash column chromatography (silica gel, ether) the corresponding ester 44 was obtained as a colourless oil; yield=2,0 g (57%); R$_f$=0,58 (silica gel, ether). IR (neat)=V=3521, 2939, 2870, 2327, 1730, 1685, 1454, 1352, 1246, 1201, 1111, 1024.

$^1$H-NMR (CDCl$_3$/TMS): δ=4,6 (1H m), 5,0 (1H m), 5,4 (2H m), 7,2 (5H m).

Step r

9a-8 Preparation of 13,14-dihydro-17-phenyl-18,19,20-trinor-PGF$_{2\alpha}$isopropyl ester 9

To a stirred solution of the above ester 43 (1,97 g, 3,25 mmol) in ethanol (25 ml) was added pyridinium-4-toluenesulfonate (0,1 g, 0,33 mmol) and the mixture was warmed to 50° C. over a period of 3 h at which time the reaction was complete (TLC monitoring). The mixture was concentrated in vacuo, the residue diluted with ethyl acetate (40 ml), washed with water (20 ml) and thereafter brine (20ml). The organic layer was dried and after flash column chromatography (silica gel, ethyl acetate) the pure product 9 was obtained as a colourless oil; yield=1,1 g (78%). R$_f$=0,24 (silica gel, EtoAc).

[α]$^{20}_D$= +42,32 (C=0,6 CH$_3$CN).

IR (neat)=V=3387, 3060, 3024, 2978, 2932, 2863, 2361, 2346, 1728, 1853, 1603, 1560, 1507, 1497, 1453, 1438, 1374, 1311, 1248, 1181, 1146, 1109, 1029, 967, 820,747, 723, 700, 665.

$^1$H-NMR (CDCl$_3$/TMS): δ=1,2 (6H d), 1,6–1,9 (10H m), 2,3 (4H t), 2,6–2,9 (4H m), 3,65 (1H m), 3,9 (1H m), 4,2 (1H m), 5,0 (1H m), 5,4 (2H m), 7,2 (5H m).

Step s

9a-9 Preparation of 13,14-dihydro-15-dehydro-17-phenyl-18,19,20-trinor-PGF$_{2\alpha}$-ipr ester 119

To a stirred solution of phenylbaric acid (0,15 g, 1,23 mmol) in dichloromethane in the presence of activated molecular sieves 4Å was added ester 9 (0,265 g, 0,61 mmol). The mixture was allowed to stand at room temperature for 20 min to form 9,11-boronate to protect 9,11-hydroxyl groups. To the boronate in dichloromethane was added pyridinium chlorochromate on alumina (328 mg, 1,52 mmol) to give the corresponding 15-alehydro analogue. After completion of the reaction ether (50 ml) was added, filtered, washed with ether, the ether layer was washed with sodium bicarbonate 5% (2×20 ml), dried on (Na$_2$SO$_4$) and evaporated in vacuo. The crude product was subjected to flash column chromatography (silica gel, ehtyl acetate:hexane 1:0,1) furnishing 119 as a colourless oil; yield=43%.

$^1$H-NMR (CDCl$_3$/TMS): δ=1,2 (6H d), 2,6 (2H t), 2,8 (2h m), 2,9 (2H m) 3,9 (1H m), 4,2 (1H m), 5,0 (1H m), 5,4 (2H m), 7,2 (5H m).

EXAMPLE 10

Preparation of 18-phenyl-19,20-trinor PGF$_{2\alpha}$-isopropyl ester (10)

Following a procedure similar to that described in example (7) with modified step 7-2. The aldehyde (12) described in 7-2 was reacted with dimethyl-2-oxo-5-phenyl pentyl phosphonate gave a crystalline substance trans-enone lactone (67% yield).

The final product 18-phenyl-19,20-dinor PGF$_{2\alpha}$-isopropy ester (10) was purified by column chromatography on silica gel-60 using ethyl acetate as eluent gave a colourless oil (41% yield).

| 1.2 (6H d)  | 5.0 (1H m) |
|-------------|------------|
| 3.95 (1H m) | 5.4 (2H m) |
| 4.10 (1H m) | 5.6 (2H q) |
| 4.20 (1H m) | 7.2 (5H m) |

EXAMPLE 11

Preparation of 19-phenyl-20-nor-PGF$_{2\alpha}$-isopropyl ester (20)

Following a procedure similar to that described in example (7) with modified step (7-2).

The aldehyde (12) described in (7-2) was reacted with dimethyl-2-oxo-6-phenyl-hexylphosphonate gave a colourless oil trans-enone lactone (56% yield).

The final product 19-phenyl-20-nor-PGF$_{2\alpha}$-isopropyl ester (20) was a colourless oil, and was purified by column chromatography on silica gel-60 using ethyl acetate as eluent (30% yield).

| Nuclear Magnetic Resonance spectrum (CDCl$_3$)- ppm: δ | |
|---|---|
| 1.2 (6H d) | 5.0 (1H m) |
| 2.6 (2H t) | 5.4 (2H m) |
| 3.9 (1H m) | 5.5 (2H t) |
| 4.1 (1H m) | 7.2 (5H m) |
| 4.2 (1H m) | |

EXAMPLE 12

Preparation of 13,14-dihydro-15-dehydro-17-phenyl-18,19,20-trinor PGF$_{2\alpha}$isopropyl ester 13,14-dihydro-17-phenyl-18,19,20-trinor PGF$_{2\alpha}$ isopropyl ester contains three hydroxyl groups (on C9, C11 and C15). Therefore selective oxidation with pyridinium chlorochromate was impossible, and the use of a proper protective group is necessary. The C$_{15}$-dehydro PG analogue was synthesised from the appropriate C$_1$-alkyl ester by initial protection of the C9 and C11 hydroxyl groups with 2 mol. excess phenylboronic acid.(Tethr. Lett. 31(1975) 2847–2850). The formation of the cyclic boronate proceeds rapidly at room temperature in the presence of activated molecular sieve to give the cyclic 9,11-boronate ester. Oxidation with pyridinium chlorochromate adsorbed on alumina proceeds very smoothly to give the protected C$_{15}$-keto ester, which was deprotected and isolated by column chromatography on silica gel 13,14-dihydro-17-phenyl-18,19,20-trinor-PGF$_{2\alpha}$ isopropyl ester (265 mg, 0,61 mmol) in dichloromethane (1 mL) was added to a solution, of phenylboronic acid (149 mg, 1,22 mmol) in dichloromethane (3 ml) in the presence of activated molecular sieve 4Å. The solution was allowed to stand at room temperature for 30 min to form the 9,11-boronate carboxylate ester. The boronate ester was directly treated with pyridinium chlorochromate (262 mg, 1,22 mmol) adsorbed on alumina (1,3 g). The mixture was then allowed to stand at room temperature for 4 h (TLC monitoring). The mixture was diluted with ether (20 ml), whereafter the solid was filtered and washed with 30×10 ml portions of ether. The combined filtrate was evaporated. The residue was then diluted with ethyl acetate (30 ml) and washed with sodium hydroxide. 0,5 N (3×10 ml) and water (20 ml). The organic layer was dried over (Na$_2$SO$_4$), and concentrated in vacuo. The residue was dissolved in THF (10 ml) followed by addition of H$_2$O$_2$ (0,5 ml) to remove the protecting group. Ethyl acetate (30 ml) was added and the mixture was washed with brine (10 ml). The organic layer was dried over sodium sulfate, concentrated and subjected to flash column chromatography (silicagel, ether) which gave the desired product as a colourless oil. Yield=53%.

R$_f$=0,46 (silicagel, EtOAc) $^1$H-NMR (CDCl$_3$/TMS): $\delta$=1,2 (d,6H), 2,3 (t,4H), 2,5 (t,2H), 2,7 (t,2H), 2,9 (t,2H), 3,8 (m, 1H), 4,2 (m, 1H), 5,0 (m, 1H), 5,4 (m,2H), 7,2 (m, 5H)

EXAMPLE 13

Preparation of 20-phenyl-PGE$_{2\alpha}$-isopropyl ester, 112

Following a procedure similar to that described in example 7a (scheme 1) with modified step 7a-2, the aldehyde 29 described in 7a-1 was reacted with dimethyl-2-oxo-7-phenyl heptyl phosphonate giving a colourless oil trans-enone lactone (40,8% yield).

The final product 20-phenyl-PGF$_{2\alpha}$-isopropyl ester 112 was a colourless oil, and was purified by column chromato-graphy on silica gel-60 using ethyl acetate as eluent (34,0% yield).

$^1$H-NMR (CDCl$_3$/TMS): $\delta$=1,2 (6H d), 2,6 (2H t), 3,9 (1H m), 4,0 (1H m) 4,1 (1H m), 5,0 (1H m), 5,4 (2H m), 5,5 (2H m), 7,2 (5H m).

EXAMPLE 14

Preparation of 20-(4-phenyl butyl) PGF$_{2\alpha}$-isopropyl ester. 113

Following a proceduce similar to that described in example 7a (scheme 1) with modified step 7a-2, the aldehyde 29 described in step 7-1 was reacted with dimethyl-2-oxo-11-phenyl undecane phosphonate and was purified by column chromatography on silica gel-60 using ethyl acetate; toluene 1:2 as eluent. A colourless oily substance was obtained (27,7% yield).

The title compound 24-phenyl-21,22,23,24-tetrahomo PGF$_{2\alpha}$-isopropyl ester 113 was obtained as an oily substance, and purified by column chromatography on silica gel-60 using ethyl acetate as eluent (45,8% yield).

$^1$H-NMR (CDCl$_3$/TMS): $\delta$=1,2 (6H d), 1,4 (4H m), 2,7 (2H t), 3,9 (1H m 4,1 (1H m), 4,2 (1H m), 5,0 (1H m), 5,4 (2H m), 5,5 (2H m), 7,2 (5H m).

EXAMPLE 15

Preparation of 17-(2-thiophene)-18,19,20-trinor-PGF$_{2\alpha}$-isopropyl ester. 114

Following a procedure similar to that described in example 1a (scheme 1) with modified step 7a-2, the aldehyde 29 described in 7a-1 was reacted with dimethyl-2-oxo-4-(2-thiophene)-butyl phosphonate giving a colourless oil trans-enone lactone (78,5% yield).

The final product 17-(2-thiophene)-18,19,20-trinor-PGF$_{2\alpha}$-isopropyl ester 114 was a colurless oil, and was purified by column chromatography on silica gel-60 using dichloro-methane:isopropanol 1:0,1 as eluent, the chromatography was repeated using ethyl acetate:hexane 1:0,5 as eluent affords a colourless oil.

$^1$H-NMR (CDCl$_3$/TMS): $\delta$=1,2 (6H d), 2,6 (2H t), 3,9 (1H m), 4,1 (1H m), 4,2 (1H m), 5,0 (1H m), 5,4 (2H m), 5,5 (2H t), 7,2 (5H m).

EXAMPLE 16

Preparation of 17-(3-thiophene)-18,19,20-trinor-PGF$_{2\alpha}$-isopropyl ester. 115

Following a procedure similar to that described in example 7a with modified step 7a-2, the aldehyde 29 described in 7a-1 was reacted with dimethyl-2-oxo-4-(3-thiophene)-butyl-phosphonate giving a colourless oil trans-enone lactone (51% yield.)

The final product 17-(3-thiophene)-18,19,20-trinor-PGF$_{2\alpha}$-isopropyl ester 115 was a colourless oil, and was purified by column chromatography on silica gel-60 using dichloro-methane:isopropanol 1:0,1 as eluent. The chromatography was repeated using ethyl acetate:-heaxne 1:0,05 as eluent ehich affords a colurless oil. The product was dried under vacuum over night.

$^1$H-NMR (CDCl$_3$/TMS): $\delta$=1,2 (6H d), 2,6 (2H t), 3,9 (1H m), 4,1 (1H m), 4,1 (1H m), 4,9 (1H m), 5,4 (2H m), 5,5 (2H m), 6,8 (2H d), 7,2 (1H m).

EXAMPLE 17 AND 18

Preparation of 17-R-methyl-17-phenyl-18,19,20-trinor-PGF$_{2\alpha}$-isopropyl ester. 116

Following a procedure similar to that described in example 7a (scheme 1) with modified step 7a-2. The aldehyde 29 described in 7a-1 was reacted with dimethyl-2-oxo-4-R,S-methyl-4-phenyl-butyl-phosphonate giving a colourless oil trans-enone lactone (61% yield).

The product 7-R,S-methyl- 17-phenyl-18,19,20-trinor-PGF$_{2\alpha}$-isopropyl ester was a colourless oil, and was purified by column chromatography on silica gel-60 using ethyl acetate as eluent. This product containing C$_{17}$ epimeric mixture was separated by preparative liquid chromatography using 38% CH$_3$CN in water V/V as eluent furnishing 116 and 117 as a colourless oil.

$^1$H-NMR (CDCl$_3$/TMS): $\delta$=1,2 (6H d), 3,7 (2H m), 4,1 (1H m), 4,9 (1H m), 5,4 (2H m), 5,5 (2H t), 7,2 (5 Hm).

EXAMPLE 19

Preparation of 17-(4-trifluoromethyl phenyl)-18,19,20-trinor-PGF$_{2\alpha}$-isopropyl ester. 118

Following a procedure similar to that described in example 7a (scheme 1) with modified step 7a-2. The aldehyde 29 described in 7a-1 was reacted with dimethyl-2-oxo-4-(4-trifluoromethyl)-phenyl-butyl-phosphonate giving a colourless oil trans-enone lactone (60% yield).

The final product 17-(4-trifluoromethyl)-phenyl-18,19,20-trinor-PGF$_{2\alpha}$-isopropyl ester 118 was a colourless oil, and was purified by column chromatography on silica gel-60 using ethyl acetate:hexane 1:0,2 as eluent (30%yield).

$^1$H-NMR (CDCl$_3$/TMS): $\delta$=1,2 (6H d), 2,6 (2H t), 3,9 (1H m), 4,1 (2H m), 5,0 (1H m), 5,4 (2H m), 5,5 (2H m), 7,3 (2H m), 7,6 (2H d).

EXAMPLE 20

Preparation of 17-(4-methylphenyl)-18,19,20-trinor-PGF$_{2\alpha}$-isopropyl ester. 120

Following a procedure similar to that described in example 7a (scheme 1) with modified step 7a-2. The aldehyde 29. described in 7a-1 was reacted with dimethyl-2-oxo-4-(4-methyl)-phenyl butyl phosphonate giving a colourless oil trans-enone lactone (61% yield).

The final product 17-(4-methyl)-phenyl-18,19,20-trinor-PGF$_{2\alpha}$-isopropyl ester 120 was a colourless oil, and was purified by column chromatography on silica gel-60 using ethyl acetate as eluent.

$^1$H-NMR (CDCl$_3$/TMS): $\delta$=1,2 (6H d), 2,6 (2H t), 3,9 (1H m), 4,1 (2H m), 5,0 (1H m), 5,4 (2H m), 5,5 (2H t), 7,1 (5H s).

EXAMPLE 21

Preparation of 17-(2-methylphenyl)-18,19,20-trinor-PGF$_{2\alpha}$-isopropyl ester. 121

Following a procedure similar to that described in example 7a (scheme 1) with modified step 7a-2, the aldehyde 29 described in 7a-1 was reacted with dimethyl-2-oxo-4-(2-methyl)-phenyl butyl phosphonate giving a colourless oil trans-enone lactone (55% yield).

The final product 17-(2-methyl)-phenyl-18,19,20-trinor-PGF$_{2\alpha}$-isopropyl ester 121 was a colourless oil, and was purified by column chromatography on silica gel-60 using ethyl acetate as eluent (20% yield).

$^1$H-NMR (CDCl$_3$/TMS): $\delta$=1,2 (6H d), 2,6 (2H m), 3,9 (1H m), 4,1 (2H m), 5,0 (1H m), 5,4 (2H m), 5,6 (2H t), 7,1 (4H m).

EXAMPLE 22

Preparation of 17-(4-fluorophenyl),18,19,20-trinor-PGF$_{2\alpha}$-ispropyl ester. 122

Following a procedure similar to that described in example 7a (scheme 1) with modified step 7a-2, the aldehyde 29 described in 7a-1 was reacted with dimethyl-2-oxo-4-(4-fluoro)-phenyl butyl phosphonate and was purified by column chromatography on silica gel-60 using ethyl acetate:toluene 1:1 as eluent.

A colourless oily substance was obtained (63% yield). The title compound 17-(4-fluoro)-phenyl-18,19,20-trinor-PGF$_{2\alpha}$-isopropyl ester 122 was obtained as an oily substance, and purified by column chromato-graphy on silica gel-60 using ethyl acetate as eluent (46% yield).

$^1$H-NMR (CDCl$_3$/TMS): $\delta$=1,2 (6H d), 2,6 (2H t), 3,9 (1H m), 4,1 (2H m), 5,0 (1H m), 5,4 (2H m), 5,5 (2H t), 6,9 (2H t), 7,1 (2H t).

EXAMPLE 23

Preparation of 20-(methylenephenyl)-PGF$_{2\alpha}$-propyl ester. 123

Following a procedure similar to that described in example 7a. (scheme 1) with modified step 7a-2, the aldehyde 29 described in 7a-1 was reacted with dimethyl-2-oxo-7-phenyl heptyl phosphonate and was purified by column chromatography on silica gel-60 using ethyl acetate:toluene 1:1 as eluent. A colourless oily substance was obtained (68% yield).

The title compound 21-phenyl-21-homo-18,19,20-trinor-PGF$_{2\alpha}$-isopropyl ester 123 was obtained as an oily substance, and purified by column chromatography on silica gel-60 using ethyl acetate:hexane 1:0,5 as eluent (26% yield).

$^1$H-NMR (CDCl$_3$/TMS): $\delta$=1,2 (6H d), 1,3 (6H m), 2,6 (2H t), 3,9 (1H m), 4,1 (1H m), 4,2 (1H m), 5,0 (1H m), 5,4 (2H m), 5,5 (2H t), 7,2 (5H m).

EXAMPLE 24

Preparation of 17-naphthyl-18,19,20-trinor-PGF$_{2\alpha}$-isopropyl ester, 124

Following a procedure similar to that described in example 7a (scheme 1) with modified step 7a-2, the aldehyde 29 described in 7a-1 was reacted with dimethyl-2-oxo-4-naphthyl-butyl-phosphonate giving a colourless oil trans-enone lactone (30% yield).

The final product 17-naphthyl-18,19,20-trinor-PGF$_{2\alpha}$-isopropyl ester 124 was a colourless oil, and was purified by column chromatography on silica gel-60 using ethyl acetateas eluent (15% yield).

$^1$H-NMR (CDCl$_3$/TMS): $\delta$=1,2 (6H d), 3,2 (2H m), 3,9 (1H m), 4,2 (2H m), 5,0 (1H m), 5,4 (2H m), 5,6 (2H t), 7,4 (4H m), 7,8 (4H m), 8,1 (1H d)

EXAMPLE 25

Preparation of 17-cyclohexyl-18,19,20-trinor-PGF$_{2\alpha}$-isopronyl ester. 125

Following a procedure similar to that described in example 7a (scheme 1) with modified step 7a-2, the aldehyde 29 described in 7a-1 was reacted with dimethyl-2-oxo-4-cyclohexyl-butyl-phosphonate giving a colourless oil trans-enone lactone (56% yield).

The final product 17-cyclohexyl-18,19,20-trinor-PGF$_{2\alpha}$-isopropyl ester 125 was a colourless oil, and was purified by column chromatography on silica gel-60 using dichloromethane: isopro-panol 1:0,1 as eluent (30% yield). The chromatography was repeated suing ethyl acetate:hexane 1:0,05 as eluent which affords a colourless oil. The product was dried under vacuum.

$^1$H-NMR (CDCl$_3$/TMS): δ=0,9 (2H m), 1,2 (4H m), 1,2 (6H d), 3,9 (1H m), 4,1 (1H 9), 4,2 (1H m), 5,0 (1H sept), 5,4 (2H m), 5,5 (2H m).

EXAMPLE 26

Preparation of 17-(4-metoxyphenyl)-18,19,20-trinor-PGF$_{2\alpha}$-isopropyl ester. 126

Following a procedure similar to that described in example 7a (scheme 1) with modified step 7a-2, the aldehyde 29 described in 7a-1 was reacted with dimethyl-2-oxo-4-(4-metoxy)-phenyl butyl phosphonate and was purified by column chromatography on silica gel-60 using ethyl acetate:toluene 1:1 as eluent. A colourless oily substance was obtained (65% yield).

The title compound 17-(4-metoxy)-phenyl-18,19,20-trinor-PGF$_{2\alpha}$-isopropyl ester 126 was obtained as an oily substance, and purified by column chromatography on silica gel-60 using ethyl acetate:hexane 1:1 as eluent (30% Field).

$^1$H-NMR (CDCl$_3$/TMS): δ=1,2 (6H d), 2,6 (2H t), 3,8 (3H s), 3,9 (1H m), 4,1 (1H m), 4,2 (b 1H m), 5,0 (1H m), 5,4 (2H m), 5,5 (2H m), 6,8 (2H d), 7,1 (2H d).

EXAMPLE 27

Preparation of 17-(3-metoxyphenyl)-18,19,20-trinor-PGF$_{2\alpha}$-isopropyl ester. 127

Following a procedure similar to that described in example 7a (scheme 1) with modified step 7a-2, the aldehyde 29 described in 7a-1 was reacted with dimethyl-2-oxo-4-(3-metoxy)-phenyl butyl phosphonate and was purified by column chromatography on silica gel-60 using ethyl acetate:toluene 1:1 as eluent. A colourless oily substance was obtained (57% yield).

The title compound 17-(3-metoxy)-phenyl-18,19,20-trinor-PGF$_{2\alpha}$-isopropyl ester 127 was obtained as an oily substance, and purified by column chromatography on silica gel-60 using ethyl acetate:hexane 1:1 as eluent (20% yield).

$^1$H-NMR (CDCl$_3$/TMS): δ=1,2 (6H d), 2,6 (2H t), 3,8 (3H s), 3,9 (1H m), 4,1 (2H m), 5,0 (1H m), 5,4 (2H m), 5,5 (2H m), 6,7 (3H t), 7,2 (1H t).

Studies of eve pressure lowering effect and adverse reactions

The intraocular pressure (IOP) was determined in animals with a pneumatonometer (Digilab Modular one TM, Bio Rad), specially calibrated for the eye of the particular species. The cornea was anaesthetized with 1-2 drops of oxibuprocain before each IOP measurement. In healthy human volunteers IOP was measured with applanation tonometry or with an air puff tonometer (Keeler pulsair). For applanation tonometry either a pneumatonometer (Digilab) or Goldmann's applanation tonometer mounted on a slit lamp microscope was used. The cornea was anaesthetized with oxibuprocain before each measurement with applanation tonometry. No local anaesthesia was employed before measurement with the pulsair tonometer.

The ocular discomfort after application of the test substances was evaluated in cats. The behaviour of cats after topical application of the test drug was followed and ocular discomfort was graded on a scale from 0 to 3, 0 indicating complete absence of any signs of discomfort, and 3 indicating maximal irritation as obvious from complete lid closure.

Conjunctival hyperemia after topical application of the test substances was evaluated in rabbits. The conjunctiva at the insertion of the superior rectus muscle of the eye was inspected or photographed with regular intervals and the degree of hyperemia was later evaluated from the color photographs in a blind manner. Conjunctival hyperemia was evaluated on a scale from 0 to 4, 0 indicating complete absence of any hyperemia, and 4 indicating marked hyperemia with conjunctival chemosis.

For determination of the effects on the intraocular pressure, primarily monkeys (cynomolgus) were employed. The reason for this is that the monkey eye is highly reminiscent of the human eye and therefor, generally, drug effects are readily extrapolated to the human eye. However, the disadvantage of using the monkey eye as a model is that the conjunctiva in this species is pigmented making it impossible to evaluate conjunctival hyperemia and furthermore, the monkey eye is relatively insensitive to irritation. Therefore, the cat eye, being very sensitive to prostaglandins was used for evaluating ocular discomfort and the rabbit eye with pronounced tendency to hyperemic reactions was used for evaluating conjunctival and episcleral hyperemia.

It is evident from Table III that modification of the omega chain of the prostaglandin skeleton introduced new and unexpected features to the prostaglandins with respect to ocular irritation (discomfort). Particularly 17-phenyl,18,19,20-trinor-PGF$_{2\alpha}$-IE and analogs were unique in exhibiting a complete loss of ocular irritation with retained IOP lowering effect in monkeys. Whereas the 17-phenyl,18,19,20-trinor-PGF$_{2\alpha}$ derivatives were extremely well tolerated, 16-phenyl-17,18,19,20-tetranor-PGF$_{2\alpha}$-IE caused clear ocular discomfort although to a lesser degree than PGF$_{2\alpha}$-IE or 15-propionate PGE$_2$-IE (Table III). However, substituting a hydrogen atom in the phenyl ring with a methoxy group having electron donating properties rendered the molecule practically free of ocular irritating effect, Table III. It is also evident from Table III that 18-phenyl-19,20,-dinor-PGF$_{2\alpha}$-IE, 19-phenyl-20-nor-PGF$_{2\alpha}$IE as well as 17-phenyl-18,19,20-trinor-PGE$_2$-IE and 13,14-dihydro-17-phenyl-18,19,20-trinor-PGA$_2$-IE, had no or very little irritating effect in the eye of cats. This indicates that the invention not only is valid for 16-, and 17-tetra- and trinor analogs of PGF$_{2\alpha}$ but for a range of omega chain modified and ring substituted analogs of PGF$_{2\alpha}$ (as exemplified with 16-phenyl-17,18,19,20-tetranor-PGF$_{2\alpha}$-IE to 19-phenyl-20-nor-PGF$_{2\alpha}$-IE), and more importantly even for different members of the prostaglandin family such as PGE$_2$ and PGA$_2$ modified in an analogous way (Table III). Thus, modifying the omega chain and substituting a carbon atom in the chain with a ring structure introduces completely new, unexpected and advantageous qualities to naturally occuring prostaglandins in that the irritating effect in the conjunctiva and cornea is abolished. In the case of 16-phenyl-17,18,19,20-tetranor-PGF$_{2\alpha}$-IE exhibiting some irritating effect substituting a hydrogen atom in the ring structure with e.g. a methoxy group attenuates or abolishes the irritating effect.

In addition to the lack of ocular discomfort the omega chain modified analogs also exhibited an advantage over naturally occuring prostalgandins in that they caused considerably less conjunctival hyperemia as studied in the rabbit eye (Table IV). Particularly, 15-dehydro-17-phenyl-18,19,20-trinor-PGF$_{2\alpha}$-IE,13,14-dihydro-17-phenyl-18,19,20-trinor-PGF$_{2\alpha}$-IE, and 13,14-dihydro-17-phenyl-18,19,20-trinor PGA$_2$-IE were adventageous in this respect. Also 18-phenyl-19,20-dinor-PGF$_{2\alpha}$-IE and 19-phenyl-20-nor-PGF$_{2\alpha}$-IE induced very little conjunctival hyperemia (Table XV).

The intraocular pressure lowering effect of omega chain modified and ring-substituted prostaglandin analogs is demonstrated in Table V. It can be seen that particularly 16-phenyl-tetranor and 17-phenyl-trinor prostaglandin analogs significantly reduced IOP in animal eyes (Table V). In all but two series of experiments cynomolgus monkeys were used. It is of particular interest to note that 17-phenyl-18,19,20-trinor PGF$_{2\alpha}$-derivatives exhibiting no ocular irritation and only modest conjunctival/episcleral hyperemia significantly lowered IOP in primates. It should furthermore be observed that both 16-phenyl-17 18 19 20-tetranor-PGF$_\alpha$-IE, 18-phenyl-19 20-dinor-PGF$_{2\alpha}$-IE and 19-phenyl-20-nor-PGF$_\alpha$-IE reduced the intraocular pressure, thus, modification of the omega chain and substituting a carbon atom in the chain with a ring structure do not render the molecule inactive with respect to the effect on the intraocular pressure.

Furthermore, it should be observed that substituting a hydrogen on the ring structure of 16-phenyl,17,18,19,20-tetranor-PGF$_{2\alpha}$-IE with a methoxy group eliminated much of the ocular irritating effect preserving most of the intraocular pressure lowering effect. Thus, omega chain modified and ring substituted prostaglandin analogs reduce IOP effectively in animals. It is further demonstrated in Table V that 16-phenoxy-17,18,19,10-tetranor-PGF$_{2\alpha}$-IE effectively lowers the intraocular pressure as studied in cats. Thus, substituting carbon 17 in the omega chain with a hetero atom, in this case oxygen, does not render the molecule inactive with respect to the effect on IOP.

It is noteworthy that most of the 17-phenyl,18,19,20-trinor-prostaglandin analogs had poor intraocular pressure lowering effect in cats, even at high doses. It is to be observed that the doses at which compounds were used presented in Table III are lower than those e.g. in Table V. Doses presented in Table III should be explicitly compared with those of the naturally occuring prostaglandins in %he same table. The same is true for Table IV. It is clear that with increasing dose side effects may increase. However, the doses of prostaglandin derivatives used in monkeys are comparatively similar to those used in human volunteers, (Table VI) being practically free of side effects.

The effect of some omega chain modified prostaglandin analogs, more specifically 17-phenyl-18,19,20-trinor-PGF$_{2\alpha}$-IE, 15-dehydro-17-phenyl-18,19,20-trinor-PGF$_{2\alpha}$-IE 15-(R)-17-phenyl-18,19,20-trinor-PGF$_{2\alpha}$-IE, 13,14-dihydro-17-phenyl-18,19,20-trinor-PGF$_{2\alpha}$-IE, and 18-phenyl-19-20-dinor-PGF$_{2\alpha}$-IE on the intraocular pressure of healthy human volunteers is demonstrated in Table VI. All compounds significantly reduced the intraocular pressure. It is particularly significant in this respect that none of the compounds had any significant irritating effect (ocular discomfort) and that 13,14-dihydro-17-phenyl-18,19,20-trinor-PGF$_{2\alpha}$-IE and 15-dehydro-17-phenyl-18 19 20-trinor-PGF$_{2\alpha}$-IE caused very little if any conjunctival/episcleral hyperemia in man. Thus, omega chain modified, and ring substituted prostaglandin analogs seem to be unique in that these compounds reduce IOP without causing significant ocular side effects such as hyperemia and discomfort.

The present invention thus describes a group of compounds exhibiting the unique property of causing insignificant ocular side effects while retaining, the intraocular pressure lowering effect. From the foregoing it is evident that the crucial modification of the molecule is a ring structure in the omega chain. Furthermore, substituents in the ring structure and/or in the omega chain may be introduced in certain molecules still exhibiting some side-effects in the eye. Hetero atoms may also be introduced into the ring substituted omega chain. Presently, particularly 17-phenyl-18,19,20-trinor-PGF$_{2\alpha}$-derivatives seem very promising for therapeutic use in glaucoma. From the scientific literature it is evident that PGE$_2$ and PGA$_2$ or their esters lower IOP in the monkey (see Bito et al, 1989). Clinical studies with PGE$_2$ have also been performed demonstrating IOP-lowering effect in man (Flach and Eliason (1988)). Thus, the analogy with PGF$_{2\alpha}$ and its esters lowering IOP in the primate eye is logic. It is most reasonable to assume that other prostaglandins with modified omega chain exhibit essentially the same properties as PGF$_{2\alpha}$ with modified omega chain, i.e. IOP lowering effect without side effects.

The results from an experiment in which the substance 13,14-dihydro-15-dehydro-17-phenyl-18,19,20-trinor-PGF$_{2\alpha}$-isopropylester, from Example 12, was administered in two healthy volunteers whereby each person received one drop of a test formulation containing 5 µg of the active substance immediately after the intraocular pressure had been measure at time 0 h. The contralateral control eye received only the vehicle. The pressure was then measured after 4, 7 and 9 hours and the following results measured with a pulsair tonometer were obtained. All the results are given in mmHg.

| Person | Eye | Time after administration | | | |
|---|---|---|---|---|---|
| | | 0 h | 4 h | 7 h | 9 h |
| 1 | Exp | 13.4 | 12.3 | 11.0 | 11.9 |
| | Contr | 13.9 | 12.2 | 12.5 | 13.4 |
| 2 | Exp | 14.0 | 12.6 | 12.3 | 11.2 |
| | Contr | 12.3 | 13.0 | 13.2 | 12.0 |

These results show that the substance indeed reduces the intraocular pressure although the starting pressures (at 0 h) in these specific examples were very low. Most strikingly, there were no side effects observed in any of the persons, neither conjunctivat hyperemia nor superficial ocular irritation in the form of grittiness or foreign body feeling.

TABLE I
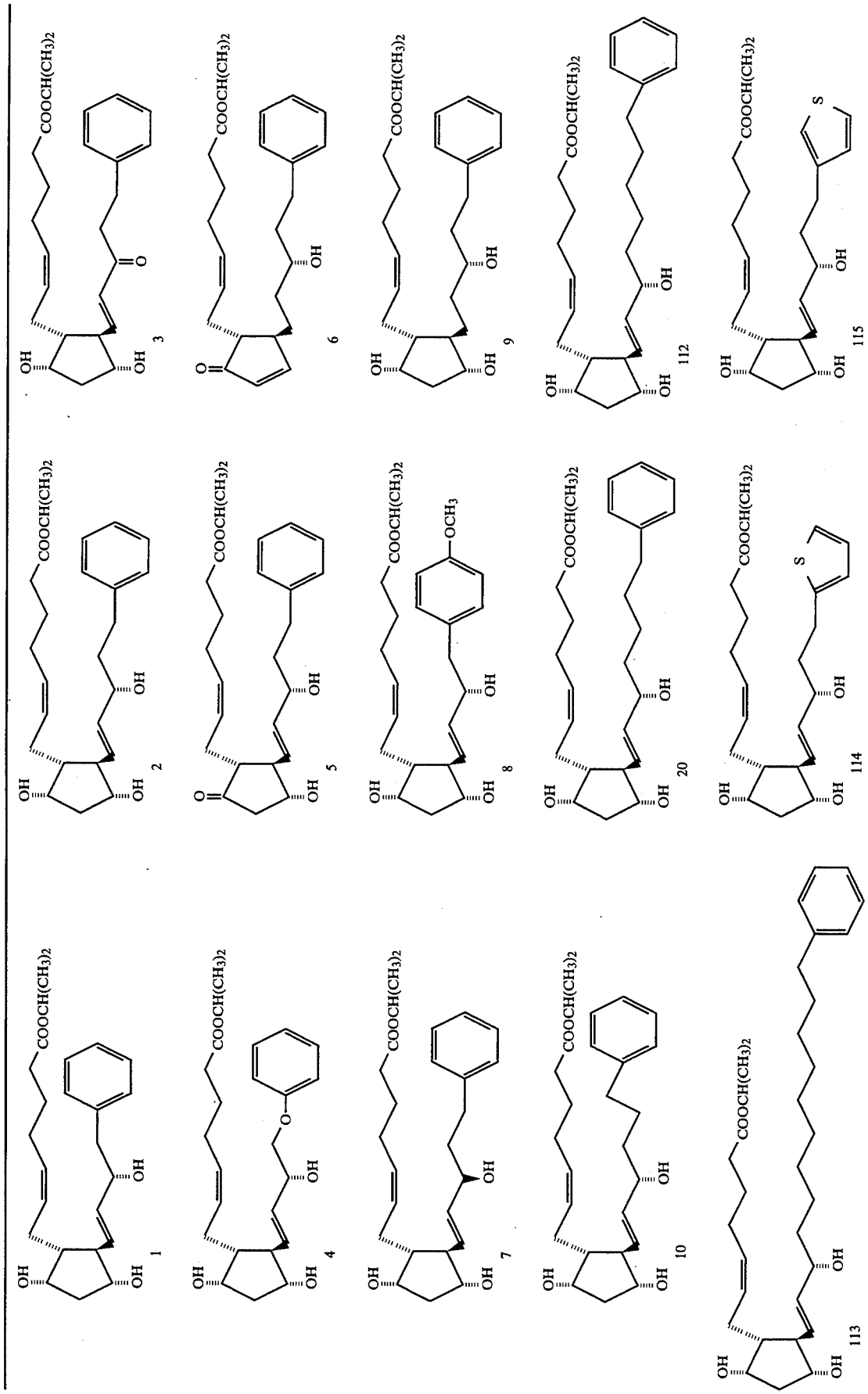

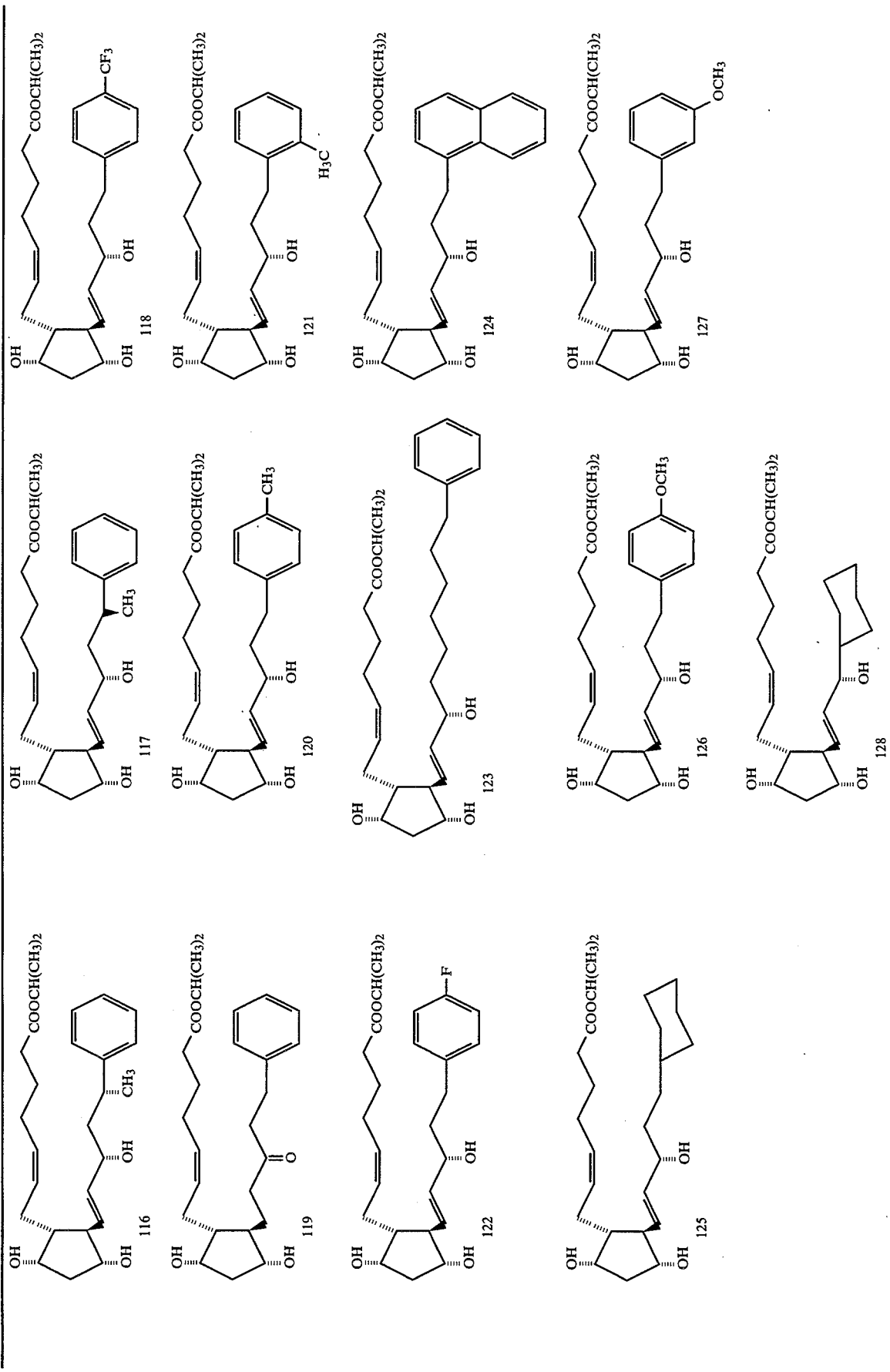

TABLE II

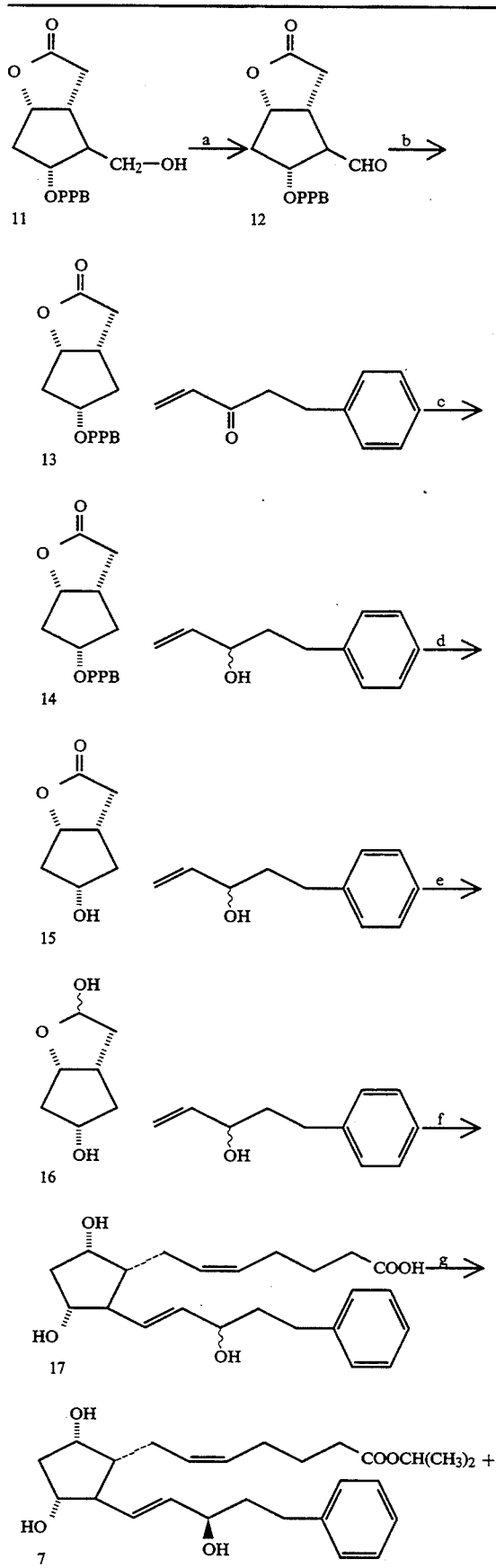

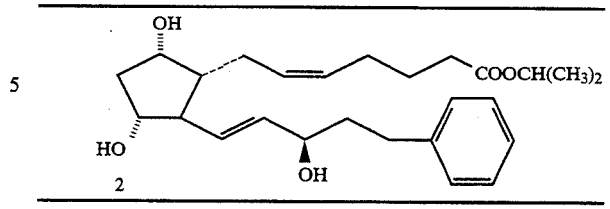

Reagents:
a DCC/DMSO/DME
b NaH/dimethyl-2-oxo-4-phenylbutyl phosphonate/DME
c CeCl$_3$.7H$_2$O/NaBH$_4$/CH$_3$−OH/−78° C.
d K$_2$CO$_3$/CH$_3$OH
e Dibal/−78° C.
f NaCH$_2$SOCH$_3$/(4-carboxybutyl)-triphenylphosphonium bromide/DMSO
g DBU/iprI/acetone

TABLE III

Irritative effect of naturally occuring prostaglandins (PGF$_{2\alpha}$, PGD$_2$ and PGE$_2$), and omega chain modified analogs applied as isopropylester on the cat eye. The avarage degree of discomfort was evaluated during 60 min after topical application of the respective test drug. The numbers within paranthesis refer to Table I.

| Substance | Dose (μg) | Degree of ocular irritation |
|---|---|---|
| PGF$_{2\alpha}$-isopropylester (-IE) | 1 | 3.0 ± 0.0 |
| 15-propionate-PGE$_2$-IE | 0.1–1 | 3.0 ± 0.0 |
| 15-propionate-PGD$_2$-IE | 1 | 1.3 ± 0.2 |
| 17-phenyl-18,19,20-trinor-PGF$_{2\alpha}$-IE (2) | 1–5 | 0 |
| 15-dehydro-17-phenyl-18,19,20-trinor-PGF$_{2\alpha}$-IE (3) | 5 | 0 |
| 15-(R)-17-phenyl-18,19,20-trinor-PGF$_{2\alpha}$-IE (7) | 1–5 | 0 |
| 13,14-dihydro-17-phenyl-18,19,20-trinor-PGF$_{2\alpha}$-IE (9) | 1 | 0 |
| 17-phenyl-18,19,20-trinor-PGE$_2$-IE (5) | 0.3 | 0 |
| 13,14-dihydro-17-phenyl-18,19,20-trinor-PGA$_2$-IE (6) | 1 | 0 |
| 16-phenyl-17,18,19,20-tetranor-PGF$_{2\alpha}$-IE (1) | 1 | 2.2 ± 0.3 |
| 16-[4-(methoxy)-phenyl]-17,18,19,20-tetranor-PGF$_{2\alpha}$-IE (8) | 1 | 0.2 ± 0.1 |
| 18-phenyl-19,20-dinor-PGF$_{2\alpha}$-IE (10) | 1 | 0.7 ± 0.1 |
| 19-phenyl-20-nor-PGF$_{2\alpha}$-IE (20) | 1 | 0.5 ± 0.1 |
| 16-phenoxy-17,18,19,20-tetranor-PGF$_{2\alpha}$-IE (4) | 5 | 0.3 ± 0.2 |

TABLE IV

Degree of conjunctival hyperemia in the rabbit eye after application of naturally occuring prostaglandins (PGF$_{2\alpha}$, and PGE$_2$), and omega chain modified analogs applied as isopropylesters.

| Substance | Dose (μg) | Degree of hyperemia |
|---|---|---|
| PGF$_{2\alpha}$-isopropylester (-IE) | 0.1 | 2.8 ± 0.2 |
| 15-propionate-PGE$_2$-IE | 0.5 | 2.7 ± 0.3 |
| 16-phenyl-17,18,19,20-tetranor-PGF$_{2\alpha}$-IE (1) | 0.5 | 1.3 ± 0.9 |
| 17-phenyl-18,19,20-trinor-PGF$_{2\alpha}$-IE (2) | 0.5 | 2.0 ± 0.3 |
| 15-dehydro-17-phenyl-18,19,20-trinor-PGF$_{2\alpha}$-IE (3) | 0.5 | 0.7 ± 0.3 |
| 15-(R)-17-phenyl-18,19,20-trinor-PGF$_{2\alpha}$-IE (7) | 0.5 | 2.0 ± 0.0 |
| 13,14-dihydro-17-phenyl-18,19,20-trinor-PGF$_{2\alpha}$-IE (9) | 0.5 | 1.3 ± 0.3 |
| 17-phenyl-18,19,20-trinor-PGE$_2$-IE (5) | 0.5 | 2.7 ± 0.2 |
| 13,14-dihydro-17-phenyl- | 0.5 | 0.3 ± 0.3 |

TABLE IV-continued

Degree of conjunctival hyperemia in the rabbit eye after application of naturally occuring prostaglandins (PGF$_{2\alpha}$, and PGE$_2$), and omega chain modified analogs applied as isopropylesters.

| Substance | Dose ($\mu$g) | Degree of hyperemia |
|---|---|---|
| 18,19,20-trinor-PGA$_2$-IE (6) | | |
| 18-phenyl-19,20-dinor-PGF$_{2\alpha}$-IE (10) | 0.5 | 0.3 ± 0.2 |
| 19-phenyl-20-nor-PGF$_{2\alpha}$-IE (20) | 0.5 | 0.2 ± 0.2 |
| 16-phenoxy-17,18,19,20-tetranor-PGF$_{2\alpha}$-IE (4) | 0.5 | 2.3 ± 0.3 |

TABLE V

Intraocular pressure reducing effect of naturally occuring prostaglandin (PGF$_{2\alpha}$) and omega chain modified analogs as determined in cynomolgus monkeys or cats. Unless specified data were obtained in monkeys. The figures within parenthesis refer to formulas given in Table I.

| Substance | Dose ($\mu$g) | 0 (mmHg) | 1–2 (mmHg) | 3–4 (mmHg) | 6 (mmHg) |
|---|---|---|---|---|---|
| PGF$_{2\alpha}$-isopropylester (IE) | 1.5 | E 11.4 ± 0.7 | 8.3 ± 0.5 * | 8.0 ± 0.6 * | 9.3 ± 0.8 |
| | | C 11.0 ± 0.7 | 10.7 ± 0.4 | 10.1 ± 0.4 | 10.6 ± 0.9 |
| 16-phenyl-17,18,19,20-tetranor-PGF$_{2\alpha}$-IE (1) | 3.2 | E 12.7 ± 1.1 | 11.8 ± 1.1 | 9.1 ± 0.8 * | 8.4 ± 0.7 * |
| | | C 12.8 ± 0.5 | 14.0 ± 0.2 | 13.0 ± 0.8 | 11.7 ± 0.8 |
| 17-phenyl-18,19,20-trinor-PGF$_{2\alpha}$-IE (2) | 3.2 | E 12.8 ± 0.6 | 11.9 ± 0.5 | 8.6 ± 0.3 * | 9.5 ± 0.7 |
| | | C 13.4 ± 0.6 | 11.7 ± 0.6 | 12.4 ± 0.2 | 11.9 ± 0.7 |
| 13,14-dihydro-17-phenyl-18,19,20-trinor-PGF$_{2\alpha}$-IE (9) | 10.4 | E 11.1 ± 0.9 | 8.3 ± 0.6 | 6.9 ± 0.4 * | 7.7 ± 0.8 |
| | | C 10.6 ± 0.7 | 8.8 ± 0.9 | 10.3 ± 1.1 | 9.5 ± 1.0 |
| 18-phenyl-19,20-dinor-PGF$_{2\alpha}$-IE (10) | 3.1 | E 9.7 ± 0.9 | 9.6 ± 1.1 | 9.6 ± 0.7 | 8.8 ± 0.9 * |
| | | C 10.1 ± 1.0 | 9.4 ± 1.2 | 9.8 ± 1.2 | 9.4 ± 0.9 |
| 16-phenoxy-17,18,19,20-tetranor-PGF$_{2\alpha}$-IE (4) | 5** | E 20.5 ± 1.2 | 25.7 ± 1.2 | 19.2 ± 1.8 | 15.0 ± 1.2 * |
| | | C 20.7 ± 1.2 | 22.7 ± 1.1 | 19.5 ± 0.9 | 19.2 ± 0.8 |
| 16-[4-(methoxy)-phenyl]-17,18,19,20-tetranor-PGF$_{2\alpha}$-IE (8) | 3.2 | E 11.2 ± 0.9 | 10.5 ± 1.3 | 9.8 ± 1.4 * | 9.2 ± 0.9 |
| | | C 10.4 ± 1.1 | 10.9 ± 1.0 | 11.3 ± 1.4 | 9.2 ± 0.6 |
| 19-phenyl-20-nor-PGF$_{2\alpha}$-IE (20) | 1** | E 16.9 ± 1.0 | 16.6 ± 0.7 | 15.8 ± 0.8 | 18.1 ± 1.2 |
| | | C 17.1 ± 0.4 | 18.1 ± 0.6 | 18.9 ± 0.6 | 19.2 ± 0.8 |

*Indicates statistical significance p < 0.05. The substances were applied topically.
**Data obtained in cat eyes.

TABLE VI

Intraocular pressure reducing effect of different omega chain modified and ring substituted PGF$_{2\alpha}$-IE analogs in healthy human volunteers. The substance number is given within paranthesis.

| Substance | Dose ($\mu$g) | n | Eye | 0 (mmHg) | 4 (mmHg) | 6 (mmHg) | 8 (mmHg) |
|---|---|---|---|---|---|---|---|
| 17-phenyl-18,19,20-trinor-PGF$_{2\alpha}$-isopropylester (IE) (2) | 1 | 4 | Exp | 11.9 ± 1.7 | 11.0 ± 0.9 * | 10.1 ± 0.7 * | 9.8 ± 0 * |
| | | | Contr | 12.7 ± 1.7 | 13.9 ± 0.7 | 13.5 ± 1.2 | 12.5 ± 0.7 |
| 15-(R)-17-phenyl-18,19,20-trinor-PGF$_{2\alpha}$-IE (7) | 10 | 3 | Exp | 12.9 ± 0.9 | 11.8 ± 0.6 | 11.0 ± 0.3 | 11.2 ± 1.3 * |
| | | | Contr | 13.2 ± 1.4 | 13.7 ± 0.9 | 13.8 ± 1.0 | 15.1 ± 1.3 |
| 15-dehydro-17-phenyl-18,19,20-trinor-PGF$_{2\alpha}$-IE (3) | 10 | 4 | Exp | 17.7 ± 0.6 | 14.6 ± 0.2 * | 13.6 ± 0.7 * | — |
| | | | Contr | 17.5 ± 0.7 | 16.4 ± 0.5 | 16.3 ± 1.0 | — |
| 13,14-dihydro-17-phenyl-18,19,20-trinor-PGF$_{2\alpha}$-IE (9) | 1 | 4 | Exp | 14.2 ± 0.5 | 13.3 ± 1.1 | 12.2 ± 0.4 * | 12.5 ± 0. |
| | | | Contr | 13.5 ± 0.6 | 14.2 ± 1.2 | 15.2 ± 1.0 | 15.1 ± 0.7 |
| 18-phenyl-19,20-dinor-PGF$_{2\alpha}$-IE (10) | 5 | 3 | Exp | 14.4 ± 1.0 | 12.2 ± 1.1 | 12.4 ± 1.2 | 11.9 ± 0.7 * |
| | | | Contr | 15.2 ± 0.1 | 13.7 ± 1.2 | 14.4 ± 0.2 | 13.2 ± 0.5 |

*Indicates statistical significance p < 0.05.

TABLE VII

Irritative effect of omega chain modified prostaglandin analogues in the cat eye. All analogues have been tested as isopropyl esters. Scale of discomfort from 0 to 3.

| Substance | Subst. no | Dose | Irritation |
|---|---|---|---|
| 24-phenyl-21,22,23,24-tetrahomo-PGF$_{2\alpha}$-isopropylester | 113 | 3.0 | 0.0 ± 0.0 |
| 17-(2-thiophene)-18,19,20-trinor-PGF$_{2\alpha}$-isopropylester | 114 | 1.0 | 0.0 ± 0.0 |
| 17-cyclohexyl-18,19,20-trinor-PGF$_{2\alpha}$-isopropylester | 125 | 1.0 | 0.3 ± 0.0 |
| 17-(4-methyl)-phenyl-18,19,20-trinor-PGF$_{2\alpha}$-isopropylester | 120 | 5.0 | 0.0 ± 0.0 |
| 17-(2-methyl)-phenyl-18,19,20-trinor-PGF$_{2\alpha}$-isopropylester | 121 | 5.0 | 0.0 ± 0.0 |
| 17-(4-trifluoromethyl)-phenyl-18,19,20-trinor-PGF$_{2\alpha}$-isopropylester | 118 | 10.0 | 0.0 ± 0.0 |
| 17-(4-fluoro)-phenyl-18,19,20-trinor-PGF$_{2\alpha}$-isopropylester | 122 | 5.0 | 0.0 ± 0.0 |
| 17-S-methyl-17-phenyl-18,19,20-trinor-PGF$_{2\alpha}$-isopropylester | 117 | 5.0 | 0.0 ± 0.0 |

TABLE VII-continued

Irritative effect of omega chain modified prostaglandin analogues in the cat eye. All analogues have been tested as isopropyl esters. Scale of discomfort from 0 to 3.

| Substance | Subst. no | Dose | Irritation |
|---|---|---|---|
| 13,14-dihydro-15-dehydro-17-phenyl-18,19,20-trinor-$PGF_{2\alpha}$-isopropylester | 119 | 5.0 | 0.0 ± 0.0 |

TABLE VIII

Effect of omega chain modified prostaglandin analogues on conjunctival hyperemia (dilatation of blood vessels in the conjunctiva of the eye) in the rabbit. All analogues have been studied as isopropyl esters and have been applied topically on the eye. Hyperemia was scored using a scale from 0 to 4.

| Substance | Subst. no | Dose | Hyperemia |
|---|---|---|---|
| $PGF_{2\alpha}$-isopropylester | — | 0.5 | 2.8 ± 0.2 |
| 24-phenyl-21,22,23,24-tetrahomo-$PGF_{2\alpha}$-isopropylester | 113 | 0.5 | 0.2 ± 0.2 |
| 17-(2-thiophene)-18,19,20-trinor-$PGF_{2\alpha}$-isopropylester | 114 | 0.5 | 1.2 ± 0.4 |
| 17-cyclohexyl-18,19,20-trinor $PGF_{2\alpha}$-isopropylester | 125 | 0.5 | 1.4 ± 0.5 |
| 17-(4-methyl)-phenyl-18,19,20-trinor $PGF_{2\alpha}$-isopropylester | 120 | 0.5 | 0.5 ± 0.3 |
| 17-(2-methyl)-phenyl-18,19,20-trinor $PGF_{2\alpha}$-isopropylester | 121 | 0.5 | 1.3 ± 0.3 |
| 17-(4-trifluoromethyl)-phenyl-18,19,20-trinor-$PGF_{2\alpha}$-isopropylester | 118 | 0.5 | 1.2 ± 0.2 |
| 17-(4-fluoro)-phenyl-18,19,20-trinor-$PGF_{2\alpha}$-isopropylester | 122 | 0.5 | 2.3 ± 0.3 |
| 17-S-methyl-17-phenyl-18,19,20-trinor-$PGF_{2\alpha}$-isopropylester | 117 | 0.5 | 1.2 ± 0.4 |
| 13,14-dihydro-15-dehydro-17-phenyl-18,19,20-trinor-$PGF_{2\alpha}$-isopropylester | 119 | 0.5 | 0.2 ± 0.2 |

TABLE IX

Effect of omega chain modified prostaglandin analogues on the intraocular pressure in normotensive unanaesthetized cynomolgus monkeys. All analogues have been tested as the isopropyl esters in aqueous solution and they have been applied in one eye while the other eye has received the vehicle only. The experimental eye has been comapred with the contralateral control (vehicle) eye.

| Substance | Dose μg | Eye | 0 h | 1 h | 2 h | 4 h | 6 h |
|---|---|---|---|---|---|---|---|
| 17-(2-thiophene)-18,19,20-trinor-$PGF_{2\alpha}$-isopropylester (114) | 3.0 | E | 13.3 ± 2.0 | 10.8 ± 0.8 | 9.3 ± 1.7 | 10.0 ± 1.1 | 11.6 ± 2.3 |
| | | C | 12.8 ± 1.9 | 11.8 ± 1.6 | 9.2 ± 1.7 | 10.0 ± 1.5 | 10.5 ± 1.7 |
| 17-cyclohexyl-18,19,20-trinor $PGF_{2\alpha}$-isopropylester (125) | 10.0 | E | 11.2 ± 1.2 | 11.3 ± 0.7 | 11.0 ± 1.0 | 10.5 ± 1.6 | 9.7 ± 1.0* |
| | | C | 11.3 ± 1.2 | 10.9 ± 0.8 | 10.0 ± 0.9 | 11.1 ± 1.2 | 11.2 ± 1.0 |
| 17-(4-methyl)-phenyl-18,19,20-trinor $PGF_{2\alpha}$-isopropylester (120) | 10.0 | E | 10.7 ± 1.3 | 9.4 ± 0.8 | 9.6 ± 0.4 | 8.6 ± 0.5* | 8.5 ± 0.2* |
| | | C | 10.4 ± 1.0 | 9.4 ± 0.8 | 9.2 ± 0.4 | 10.2 ± 0.5 | 10.7 ± 0.5 |
| 17-(2-methyl)-phenyl-18,19,20-trinor $PGF_{2\alpha}$-isopropylester (121) | 10.0 | E | 11.9 ± 0.5 | 11.3 ± 1.4 | 12.5 ± 1.5 | 9.9 ± 1.1* | 10.4 ± 0.7 |
| | | C | 11.7 ± 0.5 | 11.9 ± 1.3 | 12.5 ± 1.5 | 12.1 ± 1.1 | 10.4 ± 1.1 |
| 17-(4-trifluoromethyl)-phenyl-18,19,20-trinor-$PGF_{2\alpha}$-isopropylester (118) | 10.0 | E | 10.8 ± 1.5 | 10.7 ± 0.9 | 10.3 ± 1.3* | 9.0 ± 1.1* | 10.1 ± 1.4* |
| | | C | 10.8 ± 1.4 | 11.5 ± 1.3 | 11.4 ± 1.6 | 9.8 ± 1.1 | 11.0 ± 1.5 |
| 17-(4-fluoro)-phenyl-18,19,20-trinor-$PGF_{2\alpha}$-isopropylester (122) | 1.0 | E | 9.7 ± 1.0 | 8.9 ± 0.6 | 8.6 ± 1.0 | 6.5 ± 0.7* | 6.8 ± 0.5* |
| | | C | 9.7 ± 1.0 | 8.9 ± 0.6 | 8.8 ± 1.0 | 8.4 ± 0.9 | 9.8 ± 1.2 |
| 17-S-methyl-17-phenyl-18,19,20-trinor-$PGF_{2\alpha}$-isopropylester (117) | 10.0 | E | 11.9 ± 0.3 | 10.9 ± 1.2 | 8.8 ± 0.7 | 8.4 ± 0.6 | 8.3 ± 0.6 |
| | | C | 12.0 ± 0.4 | 10.9 ± 1.2 | 8.8 ± 0.7 | 9.3 ± 0.9 | 8.6 ± 0.6 |
| 13,14-dihydro-15-dehydro-17-phenyl-18,19,20-trinor-$PGF_{2\alpha}$-isopropylester (119) | 3.0 | E | 10.6 ± 1.3 | 9.0 ± 0.6 | 8.2 ± 1.0 | 8.9 ± 1.0 | 9.3 ± 1.1 |
| | | C | 10.6 ± 1.2 | 8.7 ± 0.7 | 8.6 ± 0.7 | 9.6 ± 0.7 | 10.0 ± 1.1 |

*: p = 0.05 (t-test)

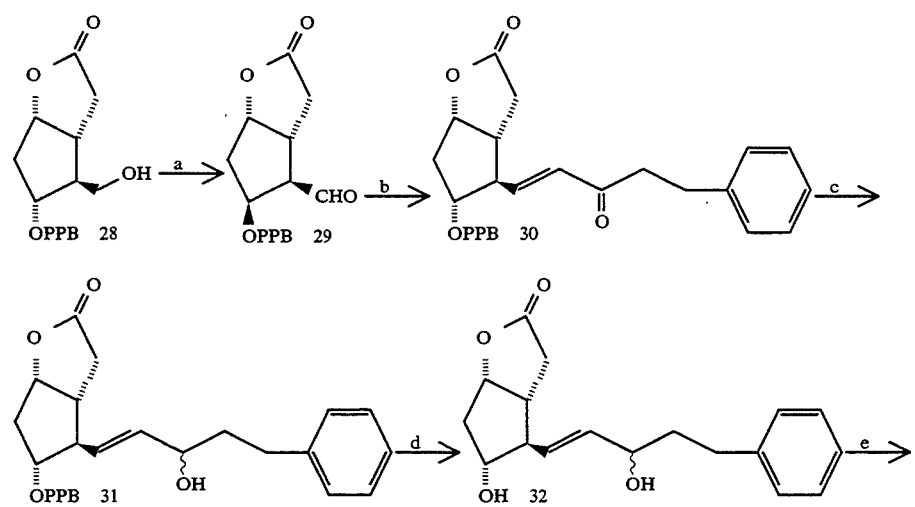

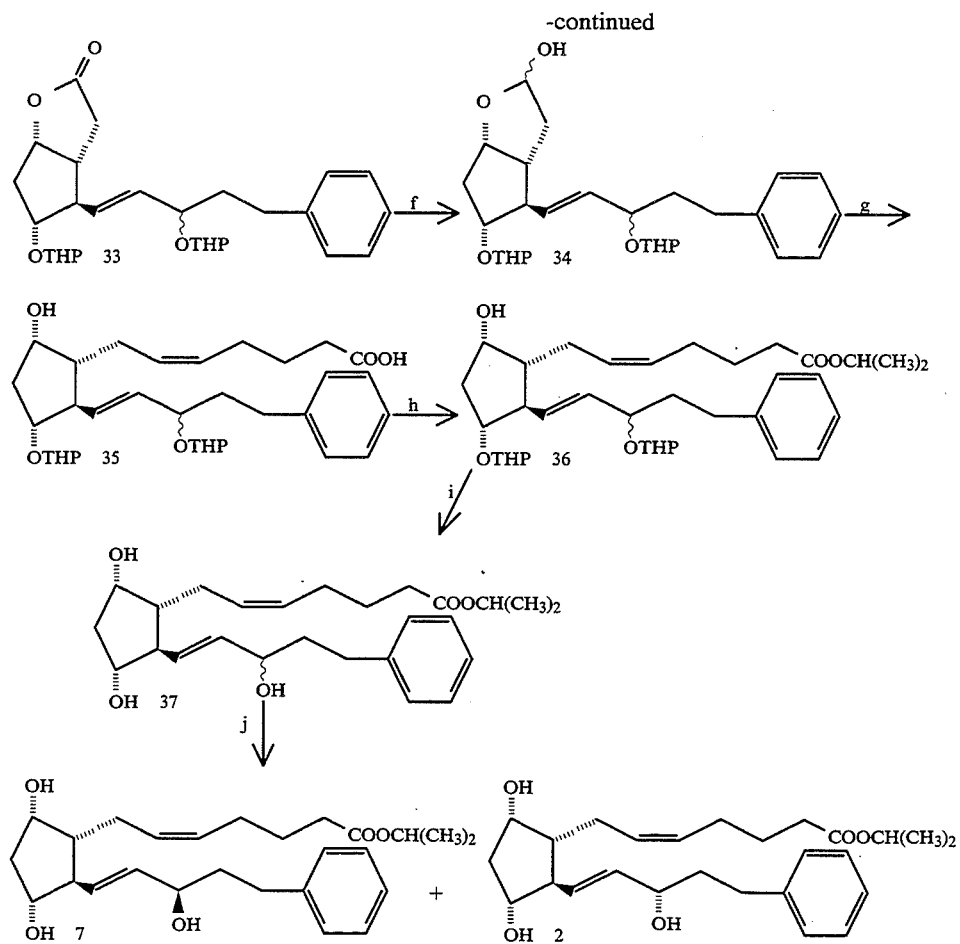
SCHEME 2
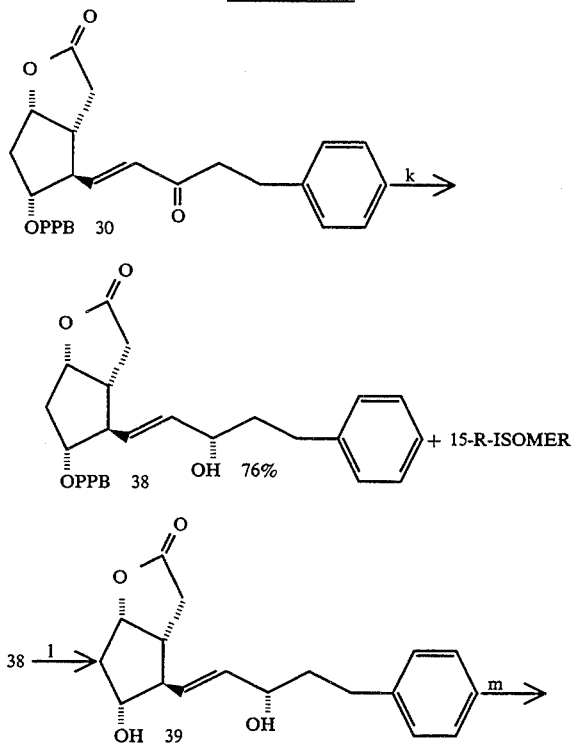
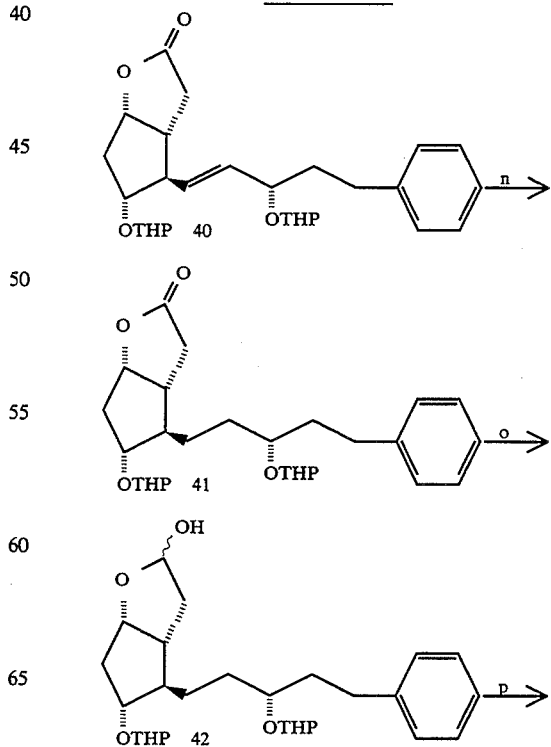

-continued
SCHEME 2

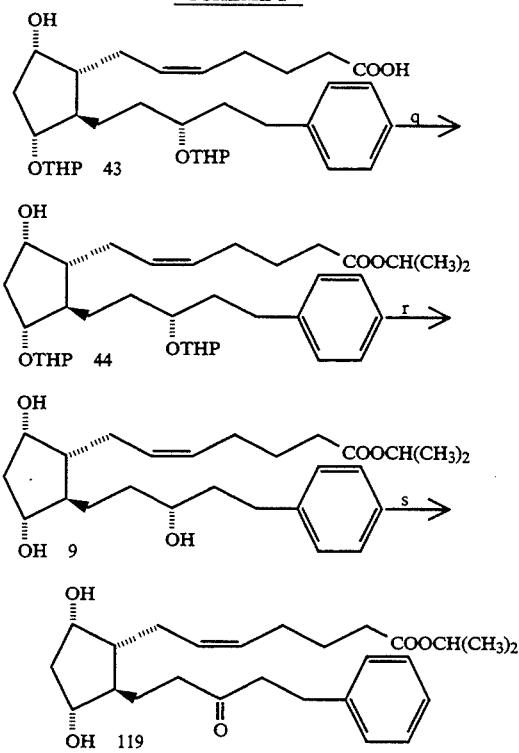

REFERENCES

Bill A (1975). Blood circulation and fluid dynamics in the eye. Physiol. Rew. 55: 383–417.

Bito L Z, Draga A, Blanco D J, Camras C B (1983). Long-term maintenance of reduced intraocular pressure by daily or twice daily topical application of prostaglandins to cat or rhesus monkey eyes. Invest Ophthalmol Vis Sci 24:312–319.

Bito L Z, Camras C B, Gum G G and Resul B (1989). The ocular hypotensive effects and side effects of prostaglandins on the eyes of experimental animals. Progress in clinical and biological research, Vol 312. Ed Laszio Z Bito and Johan Stjernschantz; Alan R Liss, Inc., New York.

Camras C B, Bito L Z (1981). Reduction of intraocular pressure in normal and glaucomatous primate (Aotus trivirgatus) eyes by topically applied prostaglandin $F_{\alpha 2}$. Curt Eye Res 1:205–209.

Camras C B, Podos S M, Rosenthal J S, Lee P Y, Severin C H (1987a). Multiple dosing of prostaglandin $F_{2\alpha}$ or epinephrine on cynomolgus monkey eyes. I. Aqueous humor dynamics. Invest Ophthalmol Vis Sci 28:463–469.

Camras C B, Bhuyan K C, Podos S M, Bhuyan D K Master R W P (1987b). Multiple dosing of prostaglandin $F_{2\alpha}$ or epinephrine on cynomolgus monkey eyes. II. Slitlamp biomicroscopy, aqueous humor analysis, and fluorescein angiography. Invest Ophthalmol Vis Sci 28:921–926.

Camras C B, Siebold E C, Lustgarten J S, Serle J B, Frisch S C, Podos S M, Bito L Z (1988). Reduction of IOP by prostaglandin $F_{2\alpha}$-1-isopropyl ester topically applied in glaucoma patients. Ophthalmology 95 (Suppl): 129.

Crawford K, Kaufman P L, and True Gabel, B'A (1987). Pilocarpine antagonizes $PGF_{2\alpha}$-induced ocular hyptension: Evidence for enhancement of uveoscleral outflow by $PGF_{2\alpha}$. Invest. Ophthalmol. Vis Sci p. 11.

Flach A J, Eliason J A (1988). Topical prostaglandin $E_2$ effects on normal human intraocular pressure. J Ocu Pharmacol 4:13–18.

Giuffré G (1985). The effects of prostaglandin $F_{2\alpha}$ in the human eye. Graefes Arch Clin Exp Ophthalmol 222: 139–141.

Kaufman P L (1986). Effects on intracamerally infused prostaglandins on outflow facility in cynomolgus monkey eyes with in%act or retrodisplaced ciliary muscle. Exp Eye Res 43:819–827.

Kerstetter J R, Brubaker R F, Wilson S E, Kullerstrand L J (1988). Prostaglandin $F_{2\alpha}$-1-isopropylester lowers intraocular pressure without decreasing aqueous humor flow. Am J Ophthalmol 105:30–34.

Lee P-Y, Shao H, Xu L, Qu C-K (1988). The effect of prostaglandin $F_{2\alpha}$ on intraocular pressure in normotensive human subjects. Invest Ophthalmol Vis Sci 29:1474–1477.

Miller W L et al (1975). Biological Activities of 17-Phenyl-18,19,20-Trinor Prostaglandins. 9 p. 9–18.

Nilsson S F E, Stjernschantz J and Bill A (1987). $PGF_{2\alpha}$ increases uveoscleral outflow. Invest. Ophthalmol. Vis Sci Suppl p. 284.

Villumsen J, Alm A (1989). Prostaglandin $F_{2\alpha}$-isopropylester eye drops. Effects in normal human eyes. Br J Ophthalmol 73: 419–426.

Pfitzner, K., E. and Mofatt, J., G.; J. Am. Chem. Soc. 87 (1965), pp 5670–5678.

Corey, E., J. and Kwiatkowski, G., T.; J. Am. Chem. Soc. 88 (1966), p 5654.

U.S. Pat. No. 4,739,078.

Brown, H., C. and Krishnamurthy, S.; J. Am. Chem. Soc. 94 (1972), pp 7159–7161.

We claim:

1. A therapeutic composition for topical treatment of ocular hypertension or glaucoma comprising a therapeutically effective amount of the isopropyl ester of 13,14-dihydro-15-dehydro-17-phenyl-18,19,20-trinor-$PGF_{2\alpha}$ in a pharmaceutically acceptable carrier.

2. A method of treating ocular hypertension or glaucoma by topical application of a composition of claim 1.

* * * * *